US010881718B2

(12) United States Patent
Berkland et al.

(10) Patent No.: US 10,881,718 B2
(45) **Date of Patent: *Jan. 5, 2021**

(54) BIFUNCTIONAL CONJUGATE COMPOSITIONS AND ASSOCIATED METHODS

(71) Applicant: THE UNIVERSITY OF KANSAS, Lawrence, KS (US)

(72) Inventors: Cory Berkland, Lawrence, KS (US); Joshua Sestak, Lawrence, KS (US); Teruna J. Siahaan, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 400 days.

This patent is subject to a terminal disclaimer.

(21) Appl. No.: 15/072,559

(22) Filed: Mar. 17, 2016

(65) Prior Publication Data

US 2017/0007684 A1 Jan. 12, 2017

Related U.S. Application Data

(63) Continuation of application No. 13/725,524, filed on Dec. 21, 2012, which is a continuation-in-part of application No. PCT/US2011/041792, filed on Jun. 24, 2011.

(60) Provisional application No. 61/358,166, filed on Jun. 24, 2010.

(51) Int. Cl.

| | |
|---|---|
| ***A61K 39/395*** | (2006.01) |
| ***A61K 39/00*** | (2006.01) |
| ***A61K 39/385*** | (2006.01) |
| ***A61K 47/54*** | (2017.01) |
| ***A61K 47/61*** | (2017.01) |
| ***A61K 47/59*** | (2017.01) |
| ***A61K 47/69*** | (2017.01) |
| ***C07B 43/00*** | (2006.01) |
| ***A61K 31/436*** | (2006.01) |

(52) U.S. Cl.
CPC ........ *A61K 39/0008* (2013.01); *A61K 31/436* (2013.01); *A61K 39/385* (2013.01); *A61K 47/549* (2017.08); *A61K 47/593* (2017.08); *A61K 47/61* (2017.08); *A61K 47/6933* (2017.08); *A61K 47/6937* (2017.08); *C07B 43/00* (2013.01); *A61K 47/6939* (2017.08); *A61K 2039/6093* (2013.01); *A61K 2039/627* (2013.01)

(58) Field of Classification Search
None
See application file for complete search history.

(56) References Cited

U.S. PATENT DOCUMENTS

| | | | | |
|---|---|---|---|---|
| 8,188,218 B2 * | 5/2012 | Siahaan | C07K 14/70503 | 435/69.7 |
| 8,956,604 B2 * | 2/2015 | Berkland | A61K 39/385 | 424/193.1 |
| 2008/0103091 A1 * | 5/2008 | Siahaan | C07K 14/4713 | 424/1.69 |
| 2010/0210509 A1 * | 8/2010 | Oh | C07K 7/06 | 514/1.1 |

* cited by examiner

*Primary Examiner* — Yunsoo Kim
(74) *Attorney, Agent, or Firm* — Robert R. Riddle; Reed Smith LLP

(57) ABSTRACT

Bifunctional conjugate compositions are provided comprising a Signal-1 moiety bound to a first polymer carrier, wherein the combined size of the Signal-1 moiety and the first polymer carrier is about 1 nanometer to about 500 nanometers; and a Signal-2 moiety bound to a second polymer carrier, wherein the combined size of the Signal-2 moiety and the second polymer carrier is about 1 nanometer to about 500 nanometers. In some embodiments, the Signal-1 moiety and the Signal-2 moiety are bound to the same polymer carrier. Associated methods are also provided.

25 Claims, 15 Drawing Sheets

A

B

C

BIFUNCTIONAL CONJUGATE COMPOSITIONS AND ASSOCIATED METHODS

CROSS REFERENCE TO RELATED APPLICATIONS

This application is a continuation of U.S. patent application Ser. No. 13/725,524 filed Dec. 21, 2012 which is a continuation-in-part of International Application No. PCT/US2011/41792, filed Jun. 24, 2011, which claims the benefit of U.S. Provisional Application No. 61/358,166, filed Jun. 24, 2010, the entire disclosures of which are incorporated herein by reference.

INCORPORATION BY REFERENCE OF A SEQUENCE LISTING

A Sequence Listing is included pursuant to 37 C.F.R. 1.821. The Sequence Listing was submitted via EFS-Web on Mar. 17, 2016. The Sequence Listing includes the text file SequenceListing.txt, which is 13 KB in size and was created on Apr. 15, 2013, and which is incorporated by reference herein in its entirety. The Sequence Listing does not include any new matter which goes beyond the disclosure of the application as filed. The attached sequence descriptions and Sequence Listing comply with the rules governing nucleotide and/or amino acid sequence disclosures in patent applications as set forth in 37 C.F.R. §§ 1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. § 1.822.

BACKGROUND

Autoimmune diseases are characterized by the proliferation of auto-reactive T cells that recognize endogenous antigens. Disease progression is generally typified by T cell activation mediated through two primary signal pathways designated Signal-1 and Signal-2. Signal-1 occurs when the T-cell antigen receptor recognizes the peptide:Major Histocompatibility Complex-II on the surface of an antigen presenting cell (APC). Thus, Signal-1 may be delivered upon the formation of a T-Cell Receptor:Major Histocompatibility Complex-peptide complex. Signal-2 may be delivered upon the binding of a Signal-2 receptor on the T cell to its protein ligand on the surface of an APC. The assembly of both the Signal-1 and Signal-2 receptors at the T cell/APC interface leads to the formation of the "immunological synapse."

Antigen recognition and the response propagated by immune cells are key events in disease progression for autoimmune and other diseases. Many of the current therapeutic approaches attempt to interfere with these events either directly or through the manipulation of secondary pathways such as cytokine production. Traditionally, these therapeutic pathways have been targeted independently; for example, monoclonal Abs targeting specific receptors (e.g. cell-adhesion or co-stimulation), altered peptide ligands or interfering with antigen presentation. Unfortunately, these treatments often lack long term efficacy or result in deleterious side effects, requiring a new therapeutic strategy.

Current therapeutic strategies, such as Copaxone® (a polymeric antigen) or allergy injections, effect Signal-1 by repeated low dose antigen exposure, thereby attempting to induce tolerance. Conversely, therapeutics targeting Signal-2 (e.g. anti-ICAM-1 or anti-LFA-1 or co-stimulatory molecules) give non-specific immunosupression and have been shown to temporarily suppresses the progression of autoimmune diseases. However, these therapies suffer from side-effects, unexpected immune responses, and a lack of specificity.

A therapeutic that combines a Signal-2 inhibitor with a disease specific antigen (Signal-1) generally may provide the ability to suppress certain autoimmune diseases or otherwise tailor immune responses; however, this type of technology currently requires a highly complex synthesis process and purification scheme. Similarly, current compositions combining antigens and Signal-2 inhibitors generally may not be available in the desired region as they tend to persist at the site of injection or go into systemic circulation.

SUMMARY

The present disclosure relates generally to bifunctional conjugate compositions and associated methods. More particularly, the present disclosure relates to bifunctional conjugate compositions that comprise a Signal-1 moiety and a Signal-2 moiety, methods of making bifunctional conjugate compositions and their use as a therapeutic for the treatment of auto-immune diseases, infectious diseases, allergies, cancers, etc.

In one embodiment, the present disclosure provides a composition comprising a Signal-1 moiety bound to a first polymer carrier, wherein the combined size of the Signal-1 moiety and the first polymer carrier is about 1 nanometer to about 500 nanometers; and a Signal-2 moiety bound to a second polymer carrier, wherein the combined size of the Signal-2 moiety and the second polymer carrier is about 1 nanometer to about 500 nanometers. In some embodiments, the Signal-1 moiety and the Signal-2 moiety are bound to the same polymer carrier.

In another embodiment, the present disclosure provides a method comprising administering to a subject in need thereof a therapeutically effective amount of composition comprising: a Signal-1 moiety bound to a first polymer carrier, wherein the combined size of the Signal-1 moiety and the first polymer carrier is about 1 nanometer to about 500 nanometers; and a Signal-2 moiety bound to a second polymer carrier, wherein the combined size of the Signal-2 moiety and the second polymer carrier is about 1 nanometer to about 500 nanometers.

In yet another embodiment, the present disclosure provides a method comprising: providing a polymer carrier comprising at least one reactive amide or aminooxy group; providing a Signal-1 moiety comprising at least one reactive amide or aminooxy group, a Signal-2 moiety comprising at least one reactive amide or aminooxy group, or both; and reacting the polymer carrier with the Signal-1 moiety, the Signal-2 moiety, or both to form a conjugate via a N-oxime bond.

The features and advantages of the present invention will be readily apparent to those skilled in the art upon a reading of the description of the embodiments that follows.

DRAWINGS

Some specific example embodiments of the disclosure may be understood by referring, in part, to the following description and the accompanying drawings.

Figures 3A, 3B, 3C:
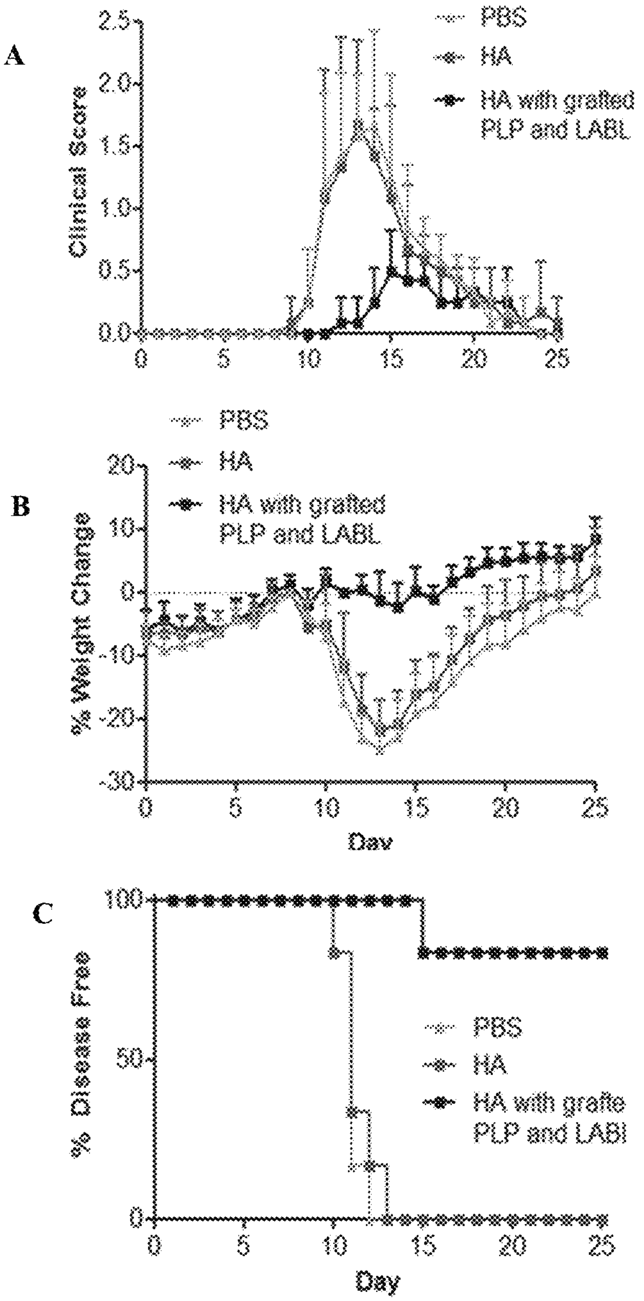

FIGS. 3A-3C are graphs showing the comparison of clinical performance of $SAgA_{LABL-PLP}$ to negative control (PBS) and polymer control (HA). The data show that $SAgA_{LABL-PLP}$ performed significantly better than controls in (A) clinical disease score, (B) % change in body weight, and (C) incidence of disease. Differences that were statistically significant are summarized in Table 6.

Figures 4A, 4B, 4C:
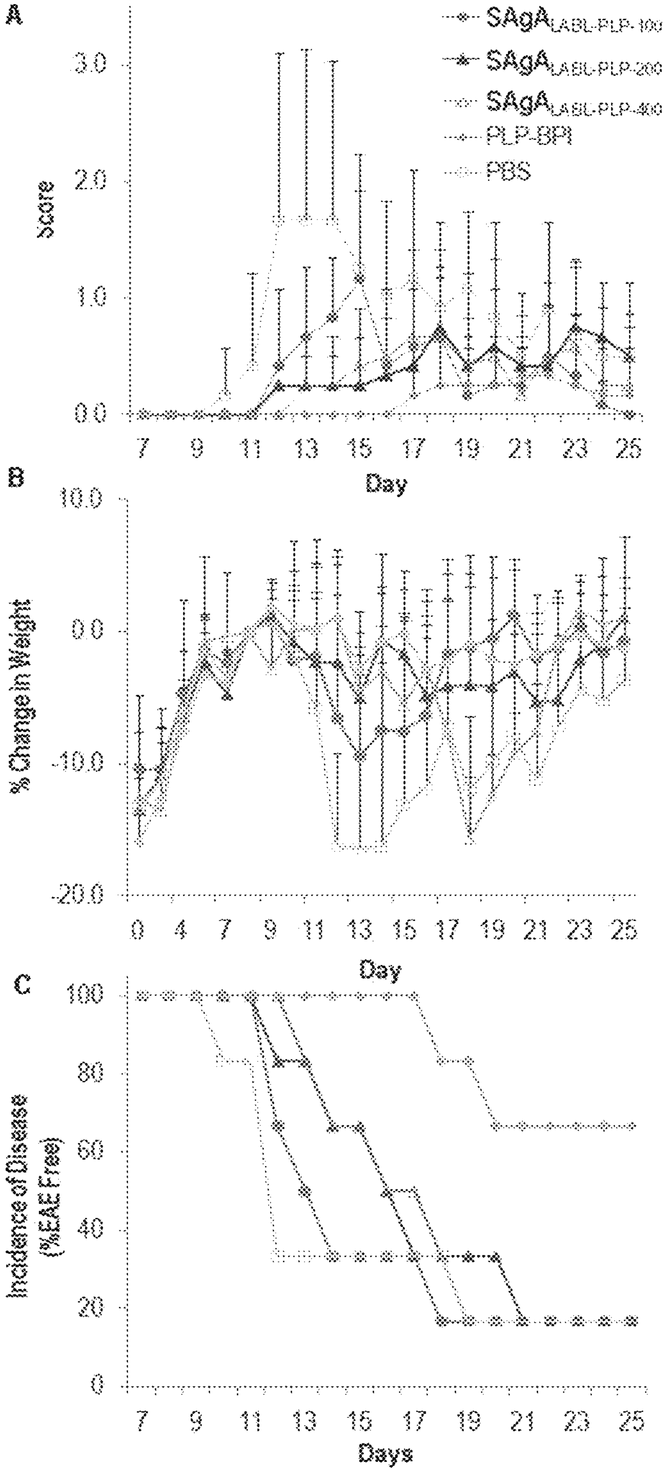

FIGS. 4A-4C are graphs depicting the effect of increasing concentration of PLP (100, 200, and 400 nMol) delivered on $SAgA_{LABL-PLP}$. The data show that 200 nMol and 400 nMol PLP dose ($SAgA_{LABL-PLP\text{-}200}$) performed best in (A) clinical disease score, (B) % change in body weight, and (C) incidence of disease. Differences that were statistically significant are summarized in Table 6.

Figures 5A, 5B, 5C:
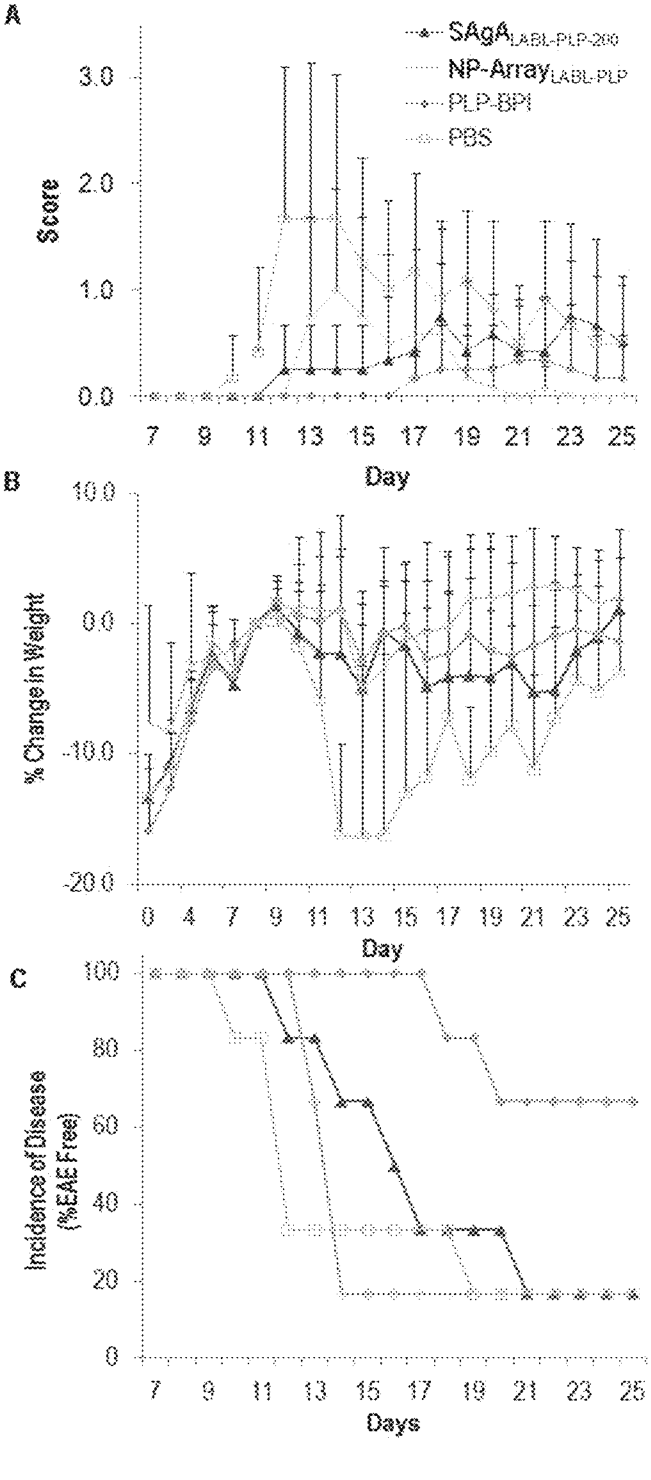

FIGS. 5A-5C are graphs depicting the effect of HA or NP scaffold on clinical efficacy. The data show that the HA array ($SAgA_{LABL-PLP\text{-}200}$) performed better than NP based array ($\text{NP-Array}_{LABL-PLP}$) in (A) clinical disease score, (B) % change in body weight, and (C) incidence of disease. Differences that were statistically significant are summarized in Table 6.

Figures 6A, 6B, 6C:
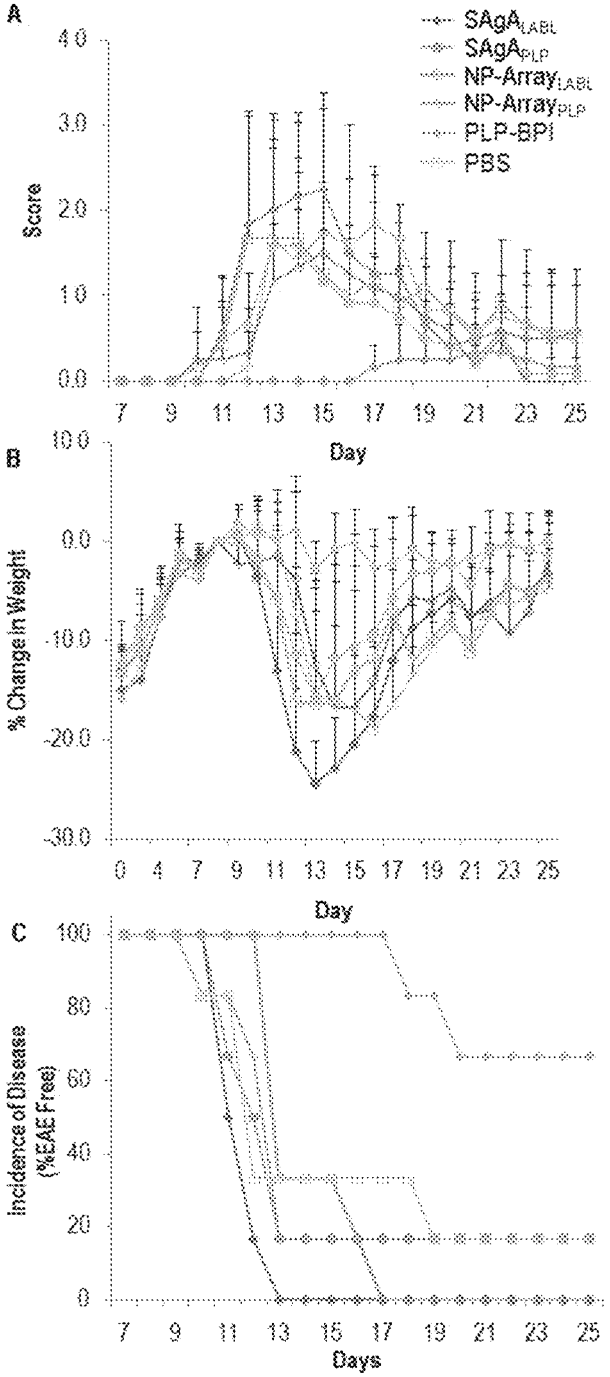

FIGS. 6A-6C are graphs depicting the effect of multivalent delivery of only antigen (PLP) or only cell adhesion inhibitor ligand (LABL) on HA or NP scaffolds. Neither the multivalent antigen nor cell adhesion inhibitor therapies provided significant suppression of disease as illustrated by overlapping (A) clinical disease score, (B) % change in body weight, and (C) incidence of disease results.

Figure 7A:
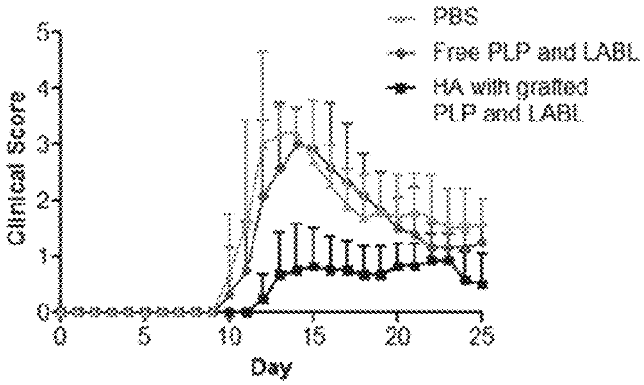
Figure 7B:
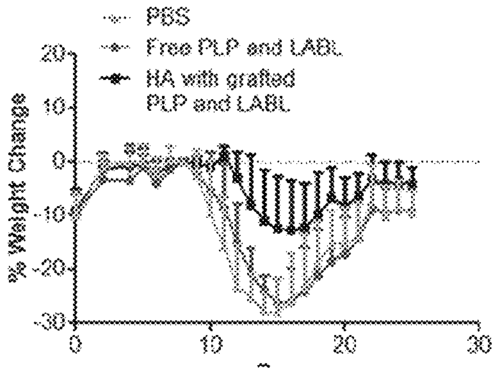
Figure 7C:
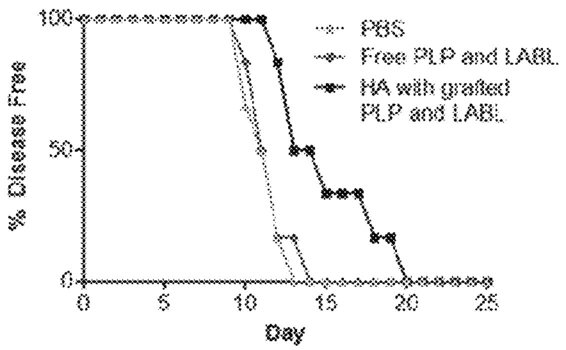

FIGS. 7A-7C are graphs depicting the effect of mixture of free LABL and PLP peptide. Mixture of free peptides provided no suppression of disease as illustrated by overlapping (A) clinical disease score, (B) % change in body weight with the negative PBS control. Incidence of disease results are also shown (C).

Figures 8A, 8B, 8C:
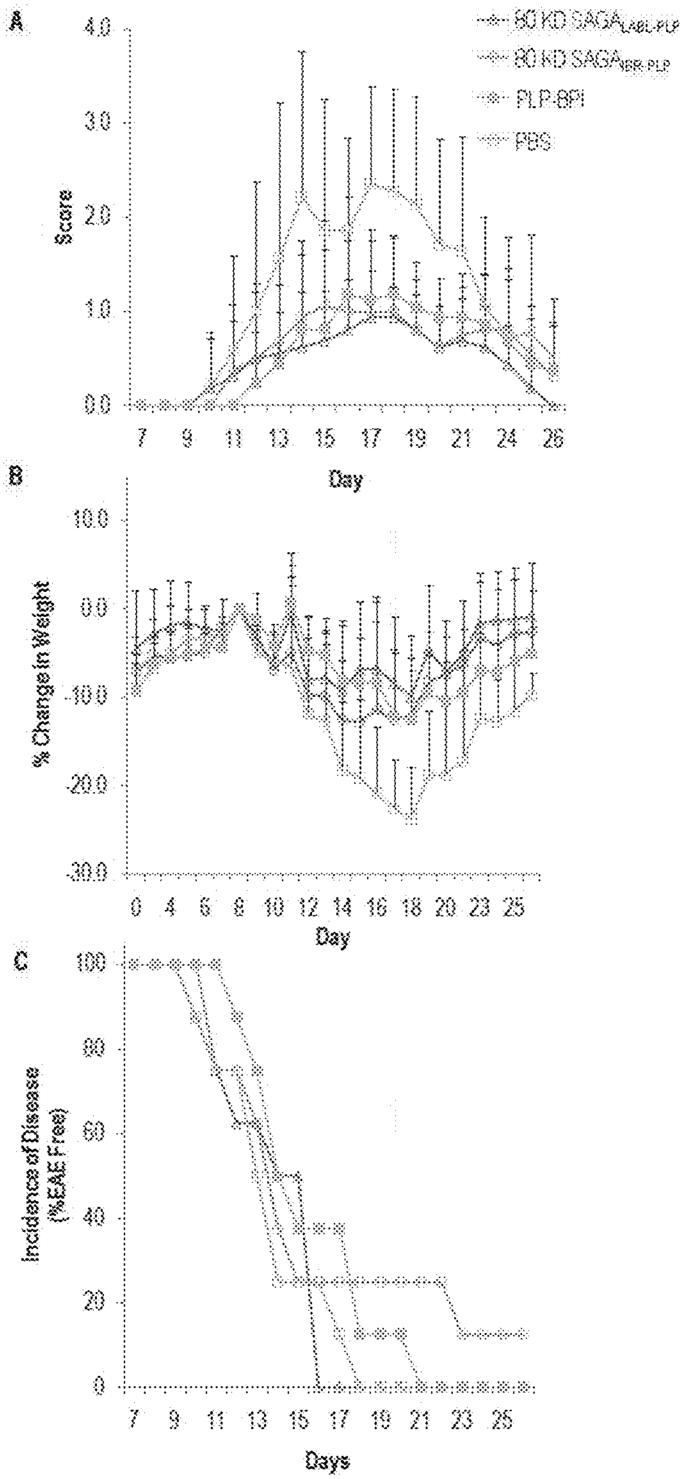

FIGS. 8A-8C are graphs depicting the effect of targeting.

Figures 9A, 9B, 9C:
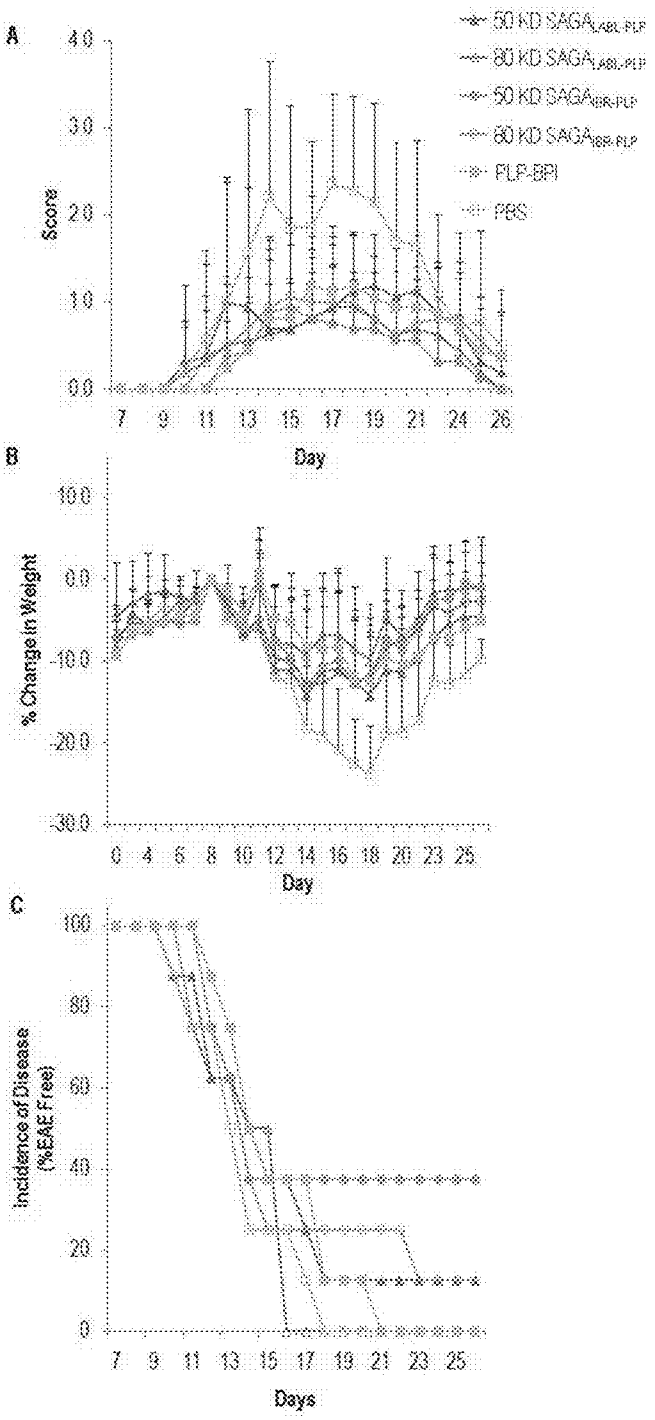

FIGS. 9A-9C are graphs depicting the effect of size on therapeutic efficacy.

Figures 10A, 10B, 10C, 10D:
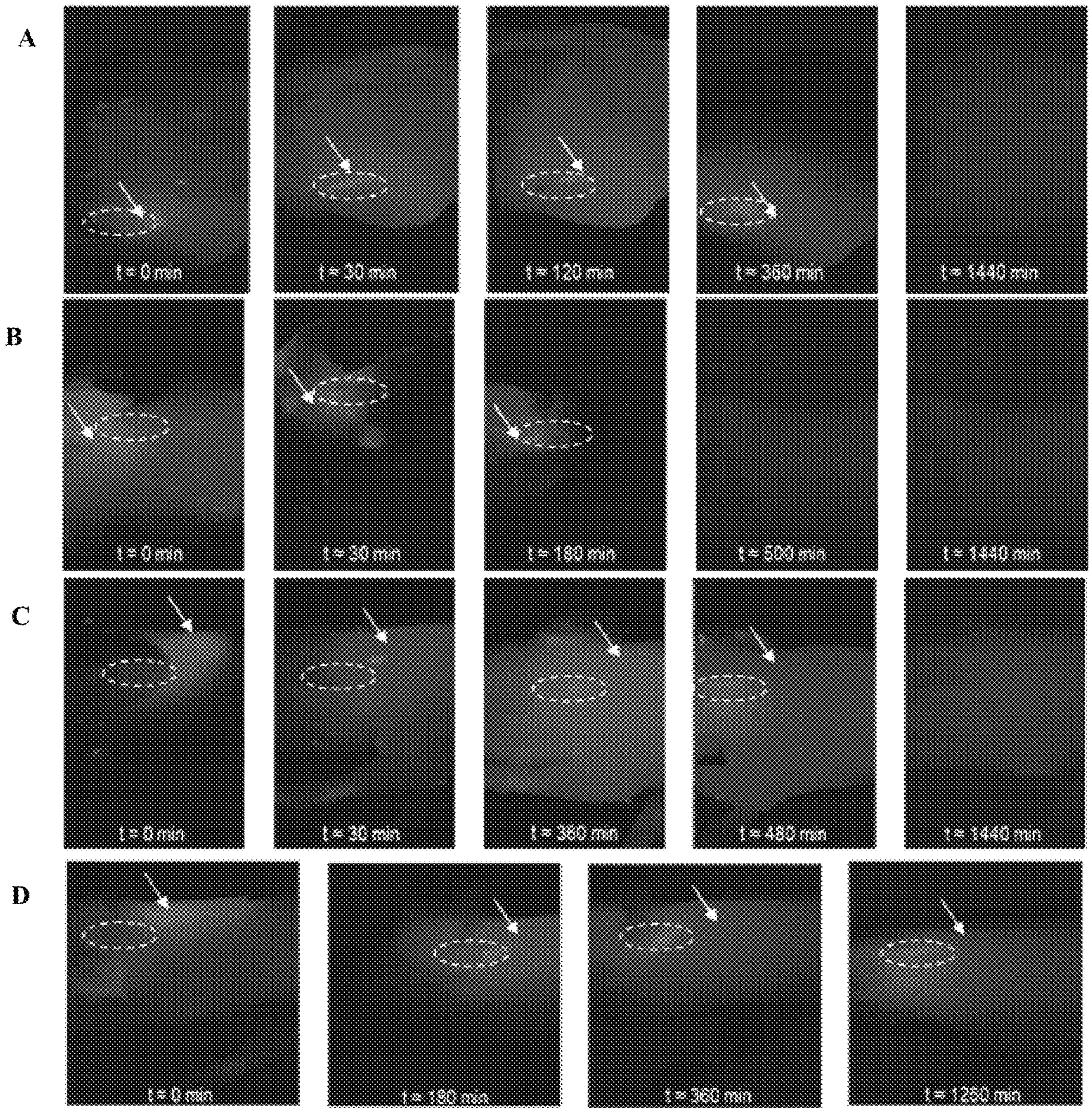
Figures 11A, 11B:
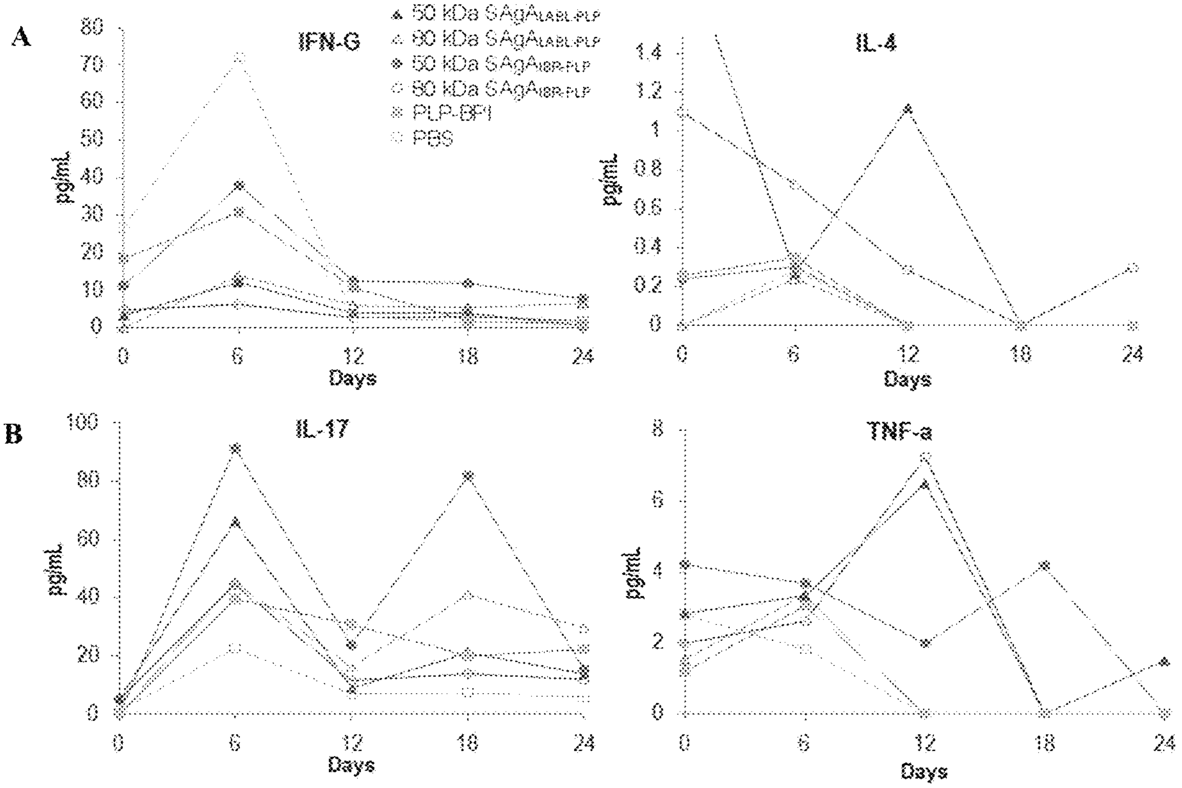

FIGS. 10A-10D depict In vivo images of mice injected with IR820-SAgAs. Injection site is indicated by arrow and the general location of lymph node packets by outlined dashed region. (A) 35 kDa HA (B) 70 kDa HA (C) 50 kDa $SAgA_{LABL-PLP}$ (D) 80 kDa $SAgA_{LABL-PLP}$ FIGS. 11A-11B depicts the cytokine profiles resulting from treatment with the indicated samples.

Figure 12:
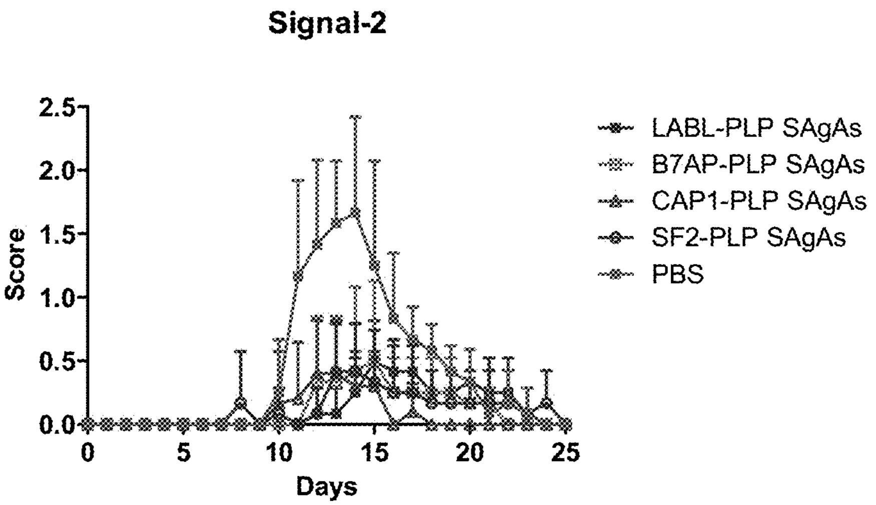

FIG. 12 shows score results showing 5 different signal-2 peptides giving significant suppression of EAE vs. PBS control. LABL-PLP, B7AP-PLP, and SF2-PLP SAgA showed significance p<0.05 days 11-15. CAP1-PLP showed significance days 11-16.

Figure 13:
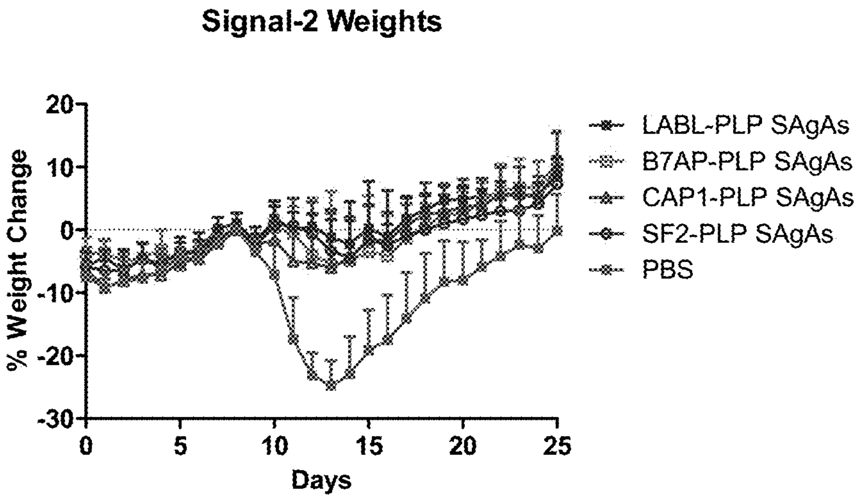

FIG. 13 shows weight data showing significant weight maintenance (P<0.05) for all treatments vs PBS on days 12-20.

Figure 14:
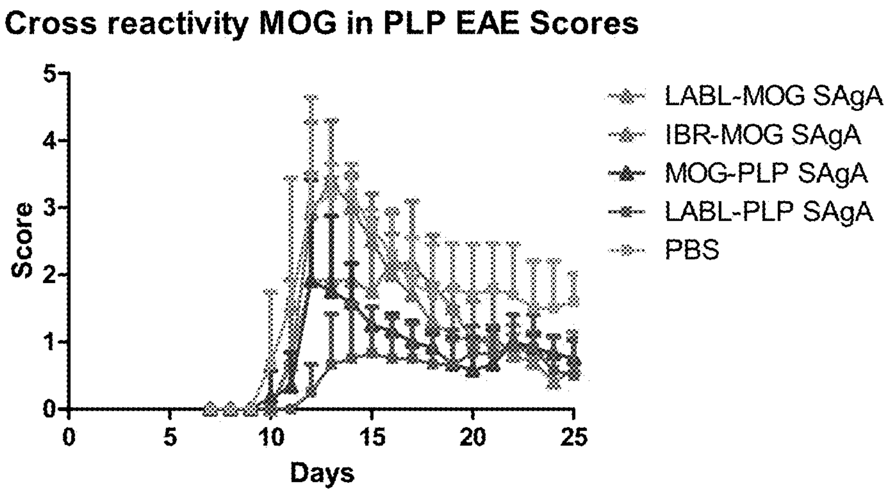

FIG. 14 shows score results showing significant suppression of PLP induced EAE using MOG-PLP SAgA (Day 14) vs. PBS control. LABL-PLP SAgA showed significance p<0.05 days 11-16.

Figure 15:
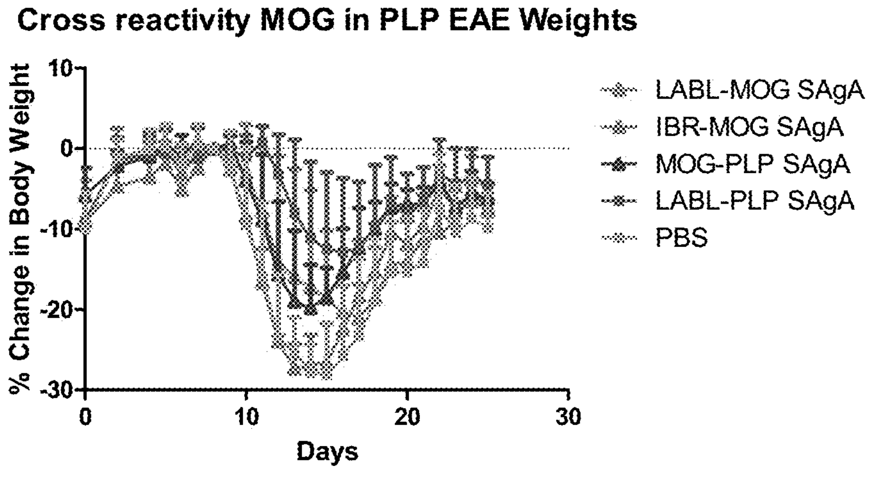

FIG. 15 shows weight data showing no significant weight maintenance of MOG SAgAs in PLP EAE model vs PBS. Significance was seen for LABL-PLP SAgA vs PBS (Days 11-15).

Figure 16:
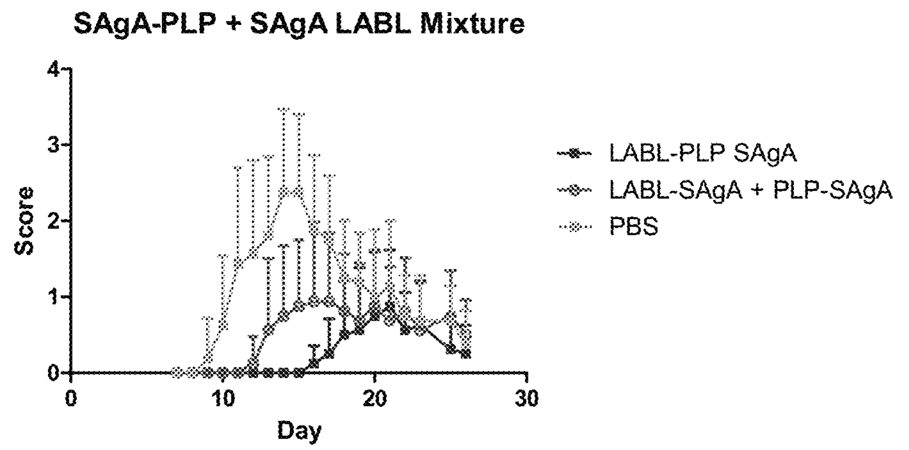

FIG. 16 shows score results showing significant suppression of EAE with mixture of LABL-SAgA and PLP-SAgA vs PBS on days 11-15.

Figure 17:
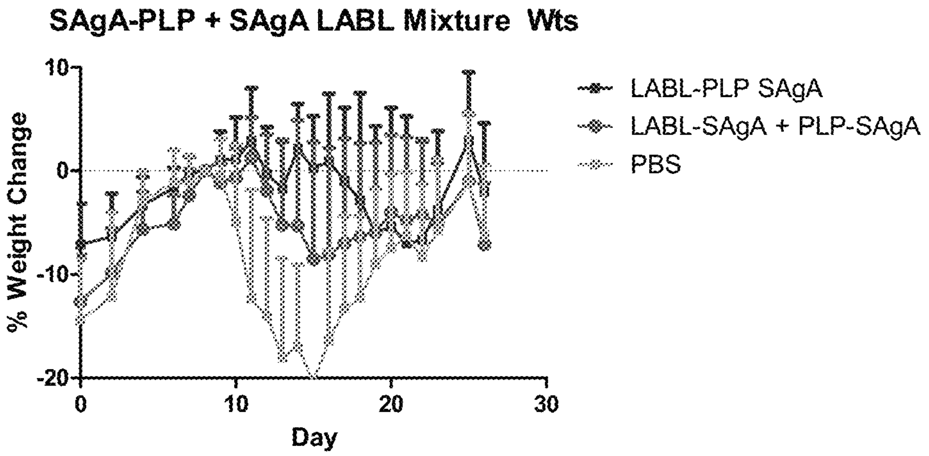

FIG. 17 shows weight data showing significant weight maintenance (P<0.05) for LABL-SAgA and PLP-SAgA vs PBS on days 11-15.

Figure 18:
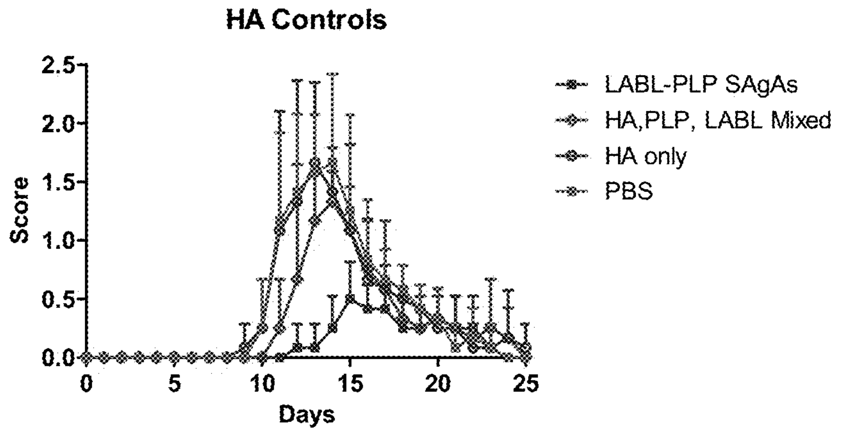

FIG. 18 shows score results indicating significant suppression of EAE with LABL-PLP SAgAs vs. polymer only (HA) on days 11-14 and a physical mixture of polymer and peptide (HA, PLP, LABL mixed) on days 13-14.

Figure 19:
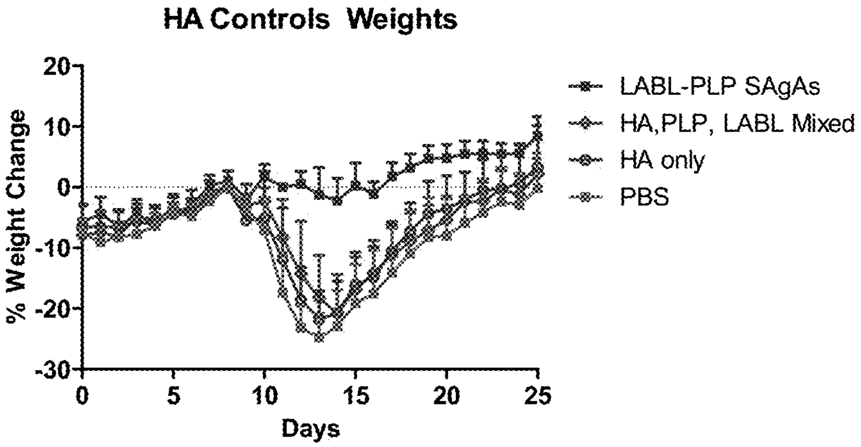

FIG. 19 shows weight data indicating significant weight maintenance (P<0.05) for LABL-PLP SAgA treatment vs all controls on days 12-20.

Figure 20:
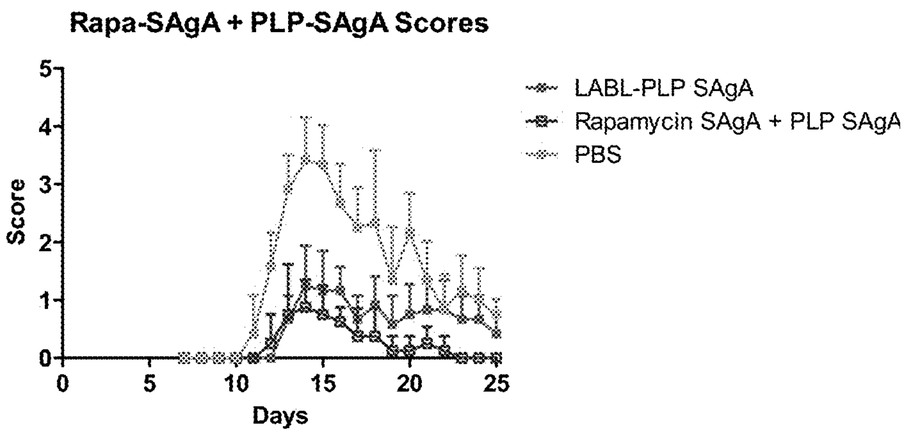

FIG. 20 illustrates score results showing significant suppression (P<0.05) of EAE with LABL-PLP SAgAs (days 12-18, and 20) and with Rapa-SAgA+PLP SAgA mixture (days 12-21, and 23) vs. PBS control.

Figure 21:
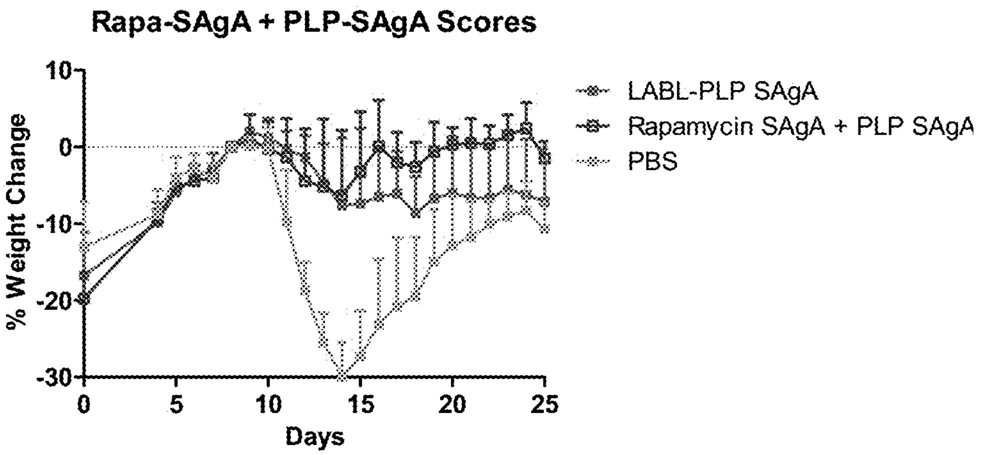

FIG. 21 illustrates weight data showing significant weight maintenance (P<0.05) for LABL-PLP SAgA (Days 12-18) and Rapa-SAgA+PLP SAgA mixture (days 12-21) treatments vs PBS Control.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure relates generally to bifunctional conjugate compositions and associated methods. More particularly, the present disclosure relates to bifunctional conjugate compositions that comprise a Signal-1 moiety and a Signal-2 moiety, methods of making bifunctional conjugate compositions, and their use as a therapeutic for the treatment of auto-immune diseases, infectious diseases, allergies, cancers, etc.

As previously mentioned above, a two-signal event must generally occur to fully activate a T cell. First, responding T cells must detect a foreign antigen on an antigen presenting cell (APC) (Signal-1). Second, the same T cell must also detect a "danger" or co-stimulatory signal, which leads to the formation of the "immunological synapse" (Signal-2). Firm, sustained adhesion between APC and T cells is necessary to form a mature immunological synapse between the cells and induce stimulation of T cells. Within the immunological synapse, antigen recognition can occur alongside a variety of co-stimulatory signals with firm adhesion mediated predominantly by LFA-1/ICAM-1. The potency of T cell activation is directly related to the number (valency), pattern, and duration of these signals.

In the past, researchers have mainly focused on discretely altering antigen exposure, blocking cell adhesion molecules, or inhibiting co-stimulation as a means to treat autoimmune diseases. For example, it is known that delivering low doses of antigen alone, either sublingually or subcutaneously, can lead to immune tolerance, however this requires delivery over a long duration and outcomes are sporadic at best. Similarly, it is also known that inhibiting cell adhesion or co-stimulatory signals temporarily suppress certain autoimmune diseases, such as type-1 diabetes, rheumatoid arthritis, and multiple sclerosis, but can also result in systemic immunosuppression. Multiple sclerosis is a relapse-remitting disease; an individual with the disease experiences attacks (also called relapses or exacerbations) of worsening neurologic functioning followed by periods of remission in which partial or complete recovery occurs.

The present disclosure is based, at least in part, on the observation that simultaneous exposure of T cells to a bifunctional conjugate composition comprising both a Signal-1 moiety and a Signal-2 moiety is believed to mitigate disease progression significantly better than either repeated low-dose antigen exposure or inhibition of immune cell adhesion or co-stimulation alone, for example. In addition, the present disclosure is also based on the observation that the physical size of the bifunctional conjugate composition is important to promote drainage from the site of injection to the lymphatic region. Accordingly, based at least in part on size, the bifunctional conjugate compositions of the present disclosure advantageously drain to the lymph nodes adjacent to the locus of the autoimmune disease, as opposed to persisting at the injection site or passing to systemic circulation.

Accordingly, in some embodiments, the present disclosure provides bifunctional conjugate compositions that can be used, inter alia, as a therapeutic for the treatment of multiple immune disease targets (e.g. vaccines for immune protection or therapeutics for treating autoimmune diseases), including, but not limited to, multiple sclerosis, rheumatoid arthritis, insulin dependent diabetes, lupus, or some asthmas, or diseases benefitting from vaccination (e.g. infectious diseases or cancer). In general, bifunctional conjugate compositions of the present disclosure may also be used as a therapeutic for the treatment of any disease state or therapeutic target (viruses, cancers) that utilizes the Signal-1 and Signal-2 proliferation pathways.

In one embodiment, the present disclosure provides bifunctional conjugate compositions that comprise at least one polymer carrier, a Signal-1 moiety, and a Signal-2 moiety. As used herein, the term "Signal-1 moiety" includes any antigen or antigen epitope (i.e., the peptide or other portion of any antigen and/or mimetics thereof to which a T cell receptor binds). As used herein, the term "Signal-2 moiety" includes a peptide and/or mimetics including small molecules known to bind to Signal-2 receptors and/or affect binding of a Signal-2 receptor to its complimentary ligand. Such Signal-2 receptors may be stimulatory or inhibitory. In some embodiments, a Signal-1 moiety and a Signal-2 moiety may be bound to the same polymer carrier or to separate polymer carriers. However, as would be recognized by one of skill in the art with the benefit of this disclosure, when a bifunctional conjugate composition comprises a Signal-1 moiety and a Signal-2 moiety bound to separate polymer carriers, the composition should be administered to a subject so as to result in the co-delivery of both a Signal-1 moiety and a Signal-2 moiety to the desired region. For example, separate Single-1 and Single-2 polymer carriers may be co-administered or administered sequentially so as to affect substantially contemporaneous delivery.

As mentioned above, the bifunctional conjugate compositions of the present disclosure are sized so as to drain to the lymph nodes adjacent to the locus of the autoimmune disease, as opposed to persisting at the injection site or entering systemic circulation. Accordingly, in those embodiments where both a Signal-1 moiety and a Signal-2 moiety are bound to one polymer carrier, the combined size of the polymer carrier, Signal-1 moiety and Signal-2 moiety is about 1 nanometers to about 500 nanometers, more preferably about 5 nanometers to about 100 nanometers, and most preferably about 10 nanometers to about 50 nanometers. In those embodiments where only a Signal-1 or Signal-2 moiety is bound to a polymer carrier, the combined size of the polymer carrier and a Signal-1 or Signal-2 moiety is about 1 nanometers to about 500 nanometers, more preferably about 5 nanometers to about 100 nanometers, and most preferably about 10 nanometers to about 50 nanometers. Furthermore, in those embodiments where only a Signal-1 or Signal-2 moiety are bound to a polymer carrier, the size of the polymer carrier for the Signal-1 moiety and the size of the polymer carrier for the Signal-2 moiety 'carriers' may be substantially similar so as to affect substantially contemporaneous delivery to the lymphatic area. In some embodiments, where a bifunctional conjugate composition comprises more than one polymer carrier, the plurality of polymer carriers may be associated via an interpenetrating network or semi-interpenetrating network.

The bifunctional conjugate compositions of the present disclosure comprise at least one polymer carrier. Polymer carriers suitable for use in the present invention include those polymers that are capable of binding a Signal-1 moiety and/or a Signal-2 moiety. Examples of suitable polymer carriers include, but are not limited to, polysaccharides, such as glycosaminoglycans (e.g., hyaluronic acid, chondroitin sulfate, dermatan sulfate, keratan sulfate, heparin, heparin sulfate, etc.) and chitosan, poly-N-vinyl formamide (PNVF), poly(ethylene glycol), poly(ethylene glycol) derivatives, polyethers and other degradable polymers such as polypeptides or polyesters. One of ordinary skill in the art with the benefit of this disclosure would be able to select an appropriate polymer carrier to be used in the bifunctional conjugate compositions of the present disclosure based on, inter alia, the type of Signal-1 moiety and/or a Signal-2 moiety which would be bound thereto.

In addition to at least one polymer carrier, the bifunctional conjugate compositions of the present disclosure comprise at least one Signal-1 moiety. In certain embodiments, the bifunctional conjugate compositions of the present disclosure comprise two or more Signal-1 moieties. Signal-1 moieties suitable for use in the compositions of the present disclosure may include a vast array of antigens or antigen epitopes. There are already many known Signal-1 moieties of interest that are defined in the literature. A partial list of some representative Signal-1 moieties include those listed in U.S. Pat. No. 7,786,257, which is hereby incorporated by reference. This list is by no means exhaustive as there are potentially thousands of Signal-1 moieties. One of ordinary skill in the art with the benefit of this disclosure would be able to select an appropriate Signal-1 moiety to be used in the bifunctional conjugate compositions of the present disclosure based on, inter alia, the type of health condition that is to be treated using the composition and/or the type of Signal-2 moiety to be used.

Examples of suitable Signal-1 moieties may include those shown in Tables 1 below:

TABLE 1

| SEQ ID No. | Sequence | Name, Source | Organism | Health Condition |
|---|---|---|---|---|
| | | Signal-1 Peptides | | |
| 1 | EIAPVFVL LE | GAD65 (208-217) | *Homo sapiens* | type-1 diabetes |
| 2 | EIAPVFVL LE | GAD67 (217-226) | *Mus musculus* | type-1 diabetes |
| 3 | QYMRADQA AGGLR | Collagen II (1168-1180) | *Homo sapiens* | rheumatoid arthritis |
| 4 | RVVINKDT TIII | *Yersinia* HSP (322-333) | *Yersinia enterocolitica* | reactive arthritis |
| 5 | ENPVVHFF KNIVTPR | Myelin BP (84-98) | *Homo sapiens* | multiple sclerosis |
| 6 | GYKVLVLN PSVAAT | HCV, NS3 (1248-61) | Hepatitis C virus | hepatitis |
| 7 | GSDTITLP CRIKQFIN MWQE | HIV, gp120 (410-429) | HIV-1 | AIDS |
| 8 | PIVQNLQG QMVHQAIS PRTL | HIV, p24 (133-152) | HIV-1 | AIDS |
| 9 | STPESANL | SIV, Tat (28-35) | Simian immunodeficiency virus | simian AIDS |
| 10 | AICKRIPN KKPGKKT | RSV, G (183-197) | Respiratory syncytial virus | asthma |
| 11 | VYRDGNPY A | HPV 16, E6 (60-68) | Human papillomavirus (HPV) | cervical cancer |
| 12 | DRAHYNI | HPV 16, E7 (48-54) | HPV | cervical cancer |
| 13 | YMLDLQPE TT | HPV 16, E7 (11-20) | HPV | cervical cancer |
| 14 | ASDLRTIQ QLLMGTV | HPV 33, E7 (73-87) | HPV | cervical cancer |
| 15 | AELYHFLL KYRAR | MAGE (3114-3126) | *Homo sapiens* | melanoma |
| 16 | LLKYRARE PVTKAE | MAGE (3120-3133) | *Homo sapiens* | melanoma |
| 17 | EQVAQYKA LPVVLENA | Fel d 1 (22-37) | *Felis domesticus* | cat allergy |
| 18 | KALPVVLE NARILKNC V | Fel d 1 (28-44) | *Felis domesticus* | cat allergy |
| 19 | LVPCAWAG NVCGEKRA YCCS | Amb a 5 (1-20) | *Ambrosia artenisiifdia* | ragweed allergy |
| 20 | PIGKYCVC YDSKAICN KNCT | Amb t 5 (21-40) | *Ambrosia trifida* | ragweed allergy |
| 21 | KSMKVTVA FNQFGPN | Cry j 1 (211-225) | *Cryptomeria japonica* | cedar allergy |
| 22 | IDIFASKN FHLQKNTI GTG | Cry j 2 (182-200) | *Cryptomeria japonica* | cedar allergy |

TABLE 1-continued

Signal-1 Peptides

| SEQ ID No. | Sequence | Name, Source | Organism | Health Condition |
|---|---|---|---|---|
| 23 | YFVGKMYFNLIDTKCYK | Phospholypase 2 (81-97) | Apis mellifera | bee allergy |
| 24 | ASEQETADATPEKEEPTAAP | Hev b 5 (37-56) | Hevia brasiliensis | latex |
| 25 | FGISNYCQIYPPNANKI | Der p 1 (111-127) | Dermatophagoides pteronyssinus | dust mites |
| 38 | MEVGWYRSPFSRVVHLYRNGK | MOG (35-55) | Mus musculus | multiple sclerosis |
| 39 | QKFSEHFSIHCCPPFTFLNSKR | MOG (16-37) | Mus musculus | multiple sclerosis |
| 40 | YGSLPQKSQRSQDENPV | MBP (68-86) | Mus musculus | multiple sclerosis |
| 41 | ASQKRPSQRSKYLATASTMD | MBP (1-20) | Mus musculus | multiple sclerosis |
| 42 | AQGTLSKIFKLGGRDSRSGSPMARR | MBP (146-170) | Mus musculus | multiple sclerosis |

The bifunctional conjugate compositions of the present disclosure additionally comprise at least one Signal-2 moiety. In certain embodiments, the bifunctional conjugate compositions of the present disclosure comprise two or more Signal-2 moieties. Signal-2 moieties suitable for use in the compositions of the present disclosure may include a vast array of peptides known to bind to Signal-2 receptors and/or affect binding of a Signal-2 receptor to its complimentary ligand on an APC. There are already many known Signal-2 moieties of interest that are defined in the literature. A partial list of some representative Signal-2 moieties include those listed in U.S. Pat. No. 7,786,257, which is hereby incorporated by reference. This list is by no means exhaustive. One of ordinary skill in the art with the benefit of this disclosure would be able to select an appropriate Signal-2 moiety to be used in the bifunctional conjugate compositions of the present disclosure based on, inter alia, the type of health condition that is to be treated using the composition and/or the type of Signal-1 moiety to be used.

Examples of suitable Signal-2 moieties include those shown in Tables 2, 3 and 4 below:

TABLE 2

Signal-2 Peptides

| SEQ ID No. | Sequence | Name, Source | Organism | Shift in Immunity |
|---|---|---|---|---|
| 26 | ITDGEATDSG | CD11a (237-247) | Homo sapiens | type-1→type-2 |
| 27 | TDGEATDSGN | CD11a (238-248) | Homo sapiens | type-1→type-2 |

TABLE 2-continued

Signal-2 Peptides

| SEQ ID No. | Sequence | Name, Source | Organism | Shift in Immunity |
|---|---|---|---|---|
| 28 | ASPGKATEVR | CTLA4 (24-33) | Homo sapiens | type-2→type-1 |
| 29 | SPSHNTDEVR | CTLA4 (24-33) | Mus musculus | type-2→type-1 |
| 30 | KVELMYPPPYYL | CTLA4 (93-104) | Homo sapiens | type-2→type-1 |
| 31 | KVELMYPPPYFV | CTLA4 (93-104) | Mus musculus | type-2→type-1 |
| 32 | ITDGEATDSG | CD11a (237-247) | Mus musculus | type-1→type-2 |
| 33 | KGYYTMSNNLVTL | CD154 (CD40L) (93-104) | Homo sapiens | type-1→type-2 |
| 34 | KGYYTMSNNLVTL | CD154 (CD40L) (93-104) | Mus musculus | type-1→type-2 |
| 35 | YMRNSKYRAGGAYGPG | Fas-ligand (CD95L) (143-155) | Homo sapiens | type-2→type-1 |
| 36 | YMRNSKYRAGGAYGPG | Fas-ligand (CD95L) (143-155) | Mus musculus | type-2→type-1 |

TABLE 2-continued

| Signal-2 Peptides | | | | |
|---|---|---|---|---|
| SEQ ID No. | Sequence | Name, Source | Organism | Shift in Immunity |
| 37 | TDGEATDS GN | CD11a (238-248) | *Mus musculus* | type-1→type-2 |
| 43 | MQPPGC | CD80-CAP1 | *Mus musculus* | type-1→type-2 |
| 44 | MAVPAT | CD80-CAP3 | *Mus musculus* | type-1→type-2 |
| 45 | GGGMQPPG C | CD80 | *Mus musculus* | type-1→type-2 |
| 46 | MYPPPYY | CD28 | *Mus musculus* | type-1→type-2 |
| 47 | EFMYPPPY LD | B7AP | *Mus musculus* | type-1→type-2 |
| 48 | GGGEFMYP PPYLD | B7 | *Mus musculus* | type-1→type-2 |
| 49 | GFVCSGIF AVGVGRC | CTLA-4/F2 | *Mus musculus* | type-2→type-1 |
| 50 | APGVRLGC AVLGRYC | CTLA-4/F6 | *Mus musculus* | type-2→type-1 |
| 51 | TEAGAAGC RGVGVAFI GSCVFG | CTLA-4 | *Mus musculus* | type-2→type-1 |
| 52 | DVC-X-X- GGPGC | CD80 | *Mus musculus* | type-1→type-2 |
| 53 | GGGPRGGV S | IBR/ICAM-1 | *Mus musculus* | type-1→type-2 |

TABLE 3

| T-cells | APC |
|---|---|
| CD28 | B7-1 (CD80) and B7-2 (CD86) |
| CTLA4 (T cell inhibitory molecule) | B7 |
| PD-1 (T cell inhibitory molecule) | PD-L1 and PDL-2 (member of B7) |
| OX40 or CD134 (TNF R superfamily) | OX40L |
| CD40L or CD154 (TNF R superfamily) | CD40 |
| LFA-1 or CD11a | ICAM-1 or CD54 |
| CD2 | LFA-3 or CD58 |
| GITR | GITRL |

TABLE 4

| T-cell | B cell | APC |
|---|---|---|
| ICOS (inducible costimulator) | B7-H2 or ICOSL | |
| CD40L or CD154 (TNF R superfamily) | CD40 | |
| | BTLA or CD272 | BTLA ligand or HNEM |
| GITR | GITRL | |
| CD30L | CD30 | |
| CD30 | CD30L | |

In some embodiments, the Single-2 moiety may comprise an immune suppressor that is capable of inhibiting or preventing activity of the immune system. In general, the immune suppressor is provided with the Signal-1 moiety. For example, the immune suppressor may be provided together with the Signal-1 moiety on a polymer carrier or provided on a separate polymer carrier independent from a Signal-1 moiety. Any immune suppressor may be suitable, including, but not limited to glucocorticoids, cytostatics, small molecules acting on immunophilins (e.g., rapamycin, ciclosporin, tacrolimus), interferons, TNF binding proteins, mycophenolate, and fingolimod. Furthermore, in some embodiments, suitable Signal-1 moieties and/or Signal-2 moieties may be glycosylated.

Signal-1 moieties and/or Signal-2 moieties suitable for use in the present disclosure may be synthesized or prepared by a number of techniques which are well known in the art. Examples include, but are not limited to, automated peptide synthesis by a robotic multiple peptide synthesizer employing Fmoc amino acid chemistry by standard methods. In these embodiments, wang resin (p-benzyloxybenzyl alcohol polystyrene) may be used as the solid support. Peptides can be characterized by reversed-phase HPLC and electrospray-mass-spectrometry. This synthesis, referred to as Merrifield peptide synthesis, utilizes traditional organic chemical reactions carried out on a solid material so that the peptide chain is lengthened while attached to the support structure. The peptides will be cleaved from the resin using TFA, and purified by reverse-phase HPLC and analyzed by mass spectroscopy. Alternatively, these reactions can be carried out in solution when larger amounts of the peptides are desired. Examples of other suitable preparation methods are well known in the art. See, for example, Creighton, 1983, Proteins: Structures and Molecular Principles, W. H. Freeman and Co., New York, which is incorporated herein by reference in its entirety. Short peptides, for example, can be synthesized on a solid support or in solution. Longer peptides maybe made using recombinant DNA techniques. Nucleotide sequences encoding peptides suitable for use in the present disclosure may be synthesized, and/or cloned, and expressed according to techniques well known to those of ordinary skill in the art. See, for example, Sambrook, et al., 1989, Molecular Cloning, A is Laboratory Manual, Vols. 1-3, Cold Spring Harbor Press, New York.

Alternatively, the peptides suitable for use in the present disclosure may be synthesized such that one or more of the bonds which link the amino acid residues of the peptides are non-peptide bonds. These alternative non-peptide bonds may be formed by utilizing reactions well known to those in the art, and may include, but are not limited to amino, ester, hydrazide, semicarbazide, and azo bonds, to name but a few. In yet another embodiment, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Purchasing preformed peptides provides another alternative source of peptides having 25 amino acids or less as these are easily purchased from commercial peptide synthesis laboratories. In later synthesis schemes, peptide mimetic compounds may be synthesized in place of the peptide moieties and linked by the same chemistry. The design of peptidomimetics is an established technique and known correlates of key amino acids of the peptide can be synthesized by previously published methods. Furthermore, as it is well known in the art, peptidomimetics may be developed which have the same modulation properties as the preferred peptides detailed herein. As these peptidomimetics require no more than routine skill in the art to produce, such peptidomimetics are embraced within the present application. Notably, the side chains of these peptidomimetics will be very similar in structure to the side chains of the preferred peptides herein, however, their peptide backbone may be very different or even entirely dissimilar. If resistance to degradation in vivo or greater conformational stability were desired, the peptides could be cyclized by any well known method. One such method adds Penicillamine (Pen) and cysteine (Cys) residues to the N- and C-termini to form cyclic peptides via a disulfide bond between the Pen and Cys residues. The formation of this cyclic peptide restricts the peptide conformation to produce a conformational stability, thereby providing better selectivity for cell surface receptors than its linear counterpart.

In some embodiments, the bifunctional conjugate compositions of the present disclosure may have defined hapten densities and/or valences, as well as concentration ratios, so as to target a range of therapeutic needs. Accordingly, in certain embodiments, a bifunctional conjugate composition of the present disclosure may have one or more of the characteristics shown in Table 5 below (Dintzis, H. M.; Dintzis, R. Z.; Vogelstein, B. Molecular determinants of immunogenicity: the immunon model of immune response. *Proc Natl Acad Sci USA* 1976, 73, (10), 3671-5). Similarly, in certain embodiments, the polymeric carrier, Signal-1 moieties and/or Signal-2 moieties of the bifunctional conjugate compositions of the present disclosure may have one or more of the characteristics discussed in U.S. Pat. Nos. 7,083,959, 6,375,951, 6,340,460, 6,022,544, 5,370,871, and 5,126,131 issued to Dintzis et al., the relevant portions of which are hereby incorporated by reference. In certain embodiments, a bifunctional conjugate composition of the present disclosure may have one or more of the immunogenic or tolerogenic characteristics shown in Table 5 below.

TABLE 5

| Polymer Properties | Immunogenic | Tolerogenic |
|---|---|---|
| Mw | >100 kDa | <100 kDa |
| Antigen Density/kDa | >10 | ~5 |
| Antigen Spacing | 2-10 nm | 2-10 nm |
| Structure | Rigid | Flexible |
| Solubility | Poorly Soluble | Soluble |

Similarly, in certain embodiments, the combined molecular weight of the polymer carrier, Signal-1 moiety and Signal-2 moiety may be less than about 500 kDa, or alternatively from about 5-100 kDa, or alternatively from about 10-50 kDa. In those embodiments where only a Signal-1 or Signal-2 moiety is bound to a polymer carrier, the combined molecular weight of the polymer carrier and a Signal-1 or Signal-2 moiety may be less than about 500 kDa, or alternatively from about 5-100 kDa, or alternatively from about 10-50 kDa. Furthermore, in those embodiments where only a Signal-1 or Signal-2 moiety are bound to a polymer carrier, the molecular weight of the polymer carrier for the Signal-1 moiety and the molecular weight of the polymer carrier for the Signal-2 moiety 'carriers' may be substantially similar so as to affect substantially contemporaneous delivery to the lymphatic area.

Furthermore, in some embodiments, the bifunctional conjugate compositions of the present disclosure may also be modified with an imaging agent or a label capable of providing a detectable signal, either directly or indirectly. Exemplary labels may include, but are not limited to, radioisotopes, fluorescent molecules, biotin and the like.

The present disclosure also provides methods of making a bifunctional conjugate composition. In one embodiment, a bifunctional conjugate composition may be prepared by conjugating a polymer carrier with a Signal-1 moiety and/or a Signal-2 moiety using conventional chemical methods such as conjugations between carboxylic acids and amines, aldehydes or ketones and amines, di-sulfide bonds, or other reactions that would be known to one skilled in the art.

In another embodiment, a bifunctional conjugate composition may be prepared using N-oxime chemistry. N-oxime chemistry provides an opportunity to conjugate a compound comprising a reactive amide group with a compound comprising a reactive aminooxy group in a specific manner due to the increased reactivity of the amino ester bond for an amide group. While not being bound by any theory, it is currently believed that the presence of the reactive aminooxy group on a compound may allow for complete de-protection of the compound prior to synthesis of a conjugate. Additional details regarding oxime chemistry may also be found in U.S. Patent Publication 2010/0047225, which is herein incorporated by reference.

Previously, it was believed that mainly aldehyde and ketone groups were reactive with aminooxy groups. However, the presence of aldehydes or ketones generally results in highly hydrophobic polymers which is undesirable. (Gajewiak 2006, Heredia 2007, Hwang 2007). A particular advantage of N-oxime chemistry is that it can be carried out in aqueous solvents and avoids many of the harsh catalysts or reaction conditions currently used to create conjugated compounds, such as multivalent polymer-peptide conjugates. Additionally, the reaction can be conducted at lowered temperatures and the reaction efficiency becomes dependent on reactant solubility providing a highly scalable process to manufacture conjugates with a high degree of haptenation (different ligands). In some embodiments, the reaction may be carried out in buffered aqueous media, at pH conditions of 4-8, and decreased temperatures, such as about 20-30° C., although a broader range of temperatures may be also be suitable. In those embodiments where a bifunctional conjugate composition is prepared using N-oxime chemistry, the methods may allow for an increased product yield, reduced purification steps, and greater product stability.

Accordingly, in some embodiments of the present disclosure, a bifunctional conjugate composition may be prepared by reacting a polymer carrier comprising at least one reactive amide or aminooxy group with a Signal-1 moiety comprising at least one reactive amide or aminooxy group, a Signal-2 moiety comprising at least one reactive amide or aminooxy group, or both to form a conjugate via a N-oxime bond. In some embodiments, the resulting conjugate may be represented by the following Formula (I):

Formula (I)

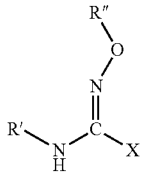

wherein R' or R" may be independently selected to be any of a number of compounds including a peptide, a protein, a polymer, a saccharide, a small molecule, a Signal-1 moiety, a Signal-2 moiety, etc. and wherein X may be H, $C_nH_{(n+2)}$ or other atoms. In some embodiments, the resulting conjugate may be represented by the following Formula (II):

Formula (II)

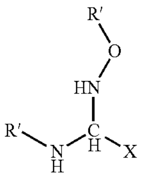

wherein R' or R" may be independently selected to be any of a number of compounds including a peptide, a protein, a polymer, a saccharide, a small molecule, a Signal-1 moiety, a Signal-2 moiety, etc. and wherein X may be H, $C_nH_{(n+2)}$ or other atoms.

In one embodiment, a polymer carrier, a Signal-1 moiety and/or a Signal-2 moiety may comprise a reactive amide group. As used herein, the term "reactive amide group" refers to an amide group that is capable of reacting with a reactive aminooxy group to form a N-oxime bond. The reactive amide group may be located anywhere on the compound provided it is still capable of reacting with a reactive aminooxy group. For example, the reactive amide group may be present in a side-chain, an end-group, or connected to the compound through one or more linkers. As will be recognized by one of ordinary skill in the art with the benefit of this disclosure, synthesis of a compound comprising a reactive amide group may be accomplished by functionalizing a desired compound (e.g., a polymer carrier, a Signal-1 moiety, a Signal-2 moiety) with an amide group through procedures well known to those of skill in the art.

Similarly, in some embodiments, a polymer carrier, a Signal-1 moiety and/or a Signal-2 moiety may comprise a reactive aminooxy group. As used herein, the term "reactive aminooxy group" refers to an aminooxy group that is capable of reacting with a reactive amide group to form a N-oxime bond. The reactive aminooxy group may be located anywhere on the compound provided it is still capable of reacting with a reactive amide group. For example, the reactive aminooxy group may be present in a side-chain, an end-group, or connected to the compound through one or more linkers. As will be recognized by one of ordinary skill in the art with the benefit of this disclosure, synthesis of a compound comprising a reactive aminooxy group may be accomplished by functionalizing a desired compound (e.g., a polymer carrier, a Signal-1 moiety, a Signal-2 moiety) with an aminooxy group through procedures well known to those of skill in the art.

In some embodiments, the present disclosure also provides pharmaceutical compositions comprising bifunctional conjugates and the use of conjugates in the manufacture of a medicament for treating a disease. Pharmaceutical compositions of the present disclosure may comprise one or more suitable pharmaceutical excipients. Standard pharmaceutical formulation techniques and excipients are well known to persons skilled in the art (see, e.g., 2005 Physicians' Desk Reference, Thomson Healthcare: Montvale, N.J., 2004; Remington: The Science and Practice of Pharmacy, 20th ed., Gennado et al., Eds. Lippincott Williams & Wilkins: Philadelphia, Pa., 2000). The compositions may or may not contain preservatives. Additionally, the pharmaceutical composition may comprise any of the conjugates described herein either as the sole active compound or in combination with another compound, composition, or biological material.

The formulation of pharmaceutical compositions may vary depending on the intended route of administrations and other parameters (see, e.g., Rowe et al. Handbook of Pharmaceutical Excipients, 4th ed., APhA Publications, 2003.) Administration of a pharmaceutical composition of the present disclosure is not limited to any particular delivery system and may include, without limitation, parenteral (including subcutaneous, intravenous, intracranial, intramedullary, intraarticular, intramuscular, intrathecal, or intraperitoneal injection), transdermal, or oral (for example, in capsules, suspensions, or tablets). Administration to an individual may occur in a single dose or in repeat administrations, and in any of a variety of physiologically acceptable salt forms, and/or with an acceptable pharmaceutical carrier and/or additive as part of a pharmaceutical composition.

The bifunctional conjugate compositions described herein are administered in therapeutically effective amounts. Generally, a therapeutically effective amount may vary with the subject's age, condition, and sex, as well as the severity of the medical condition in the subject. The dosage may be determined by a physician and adjusted, as necessary, to suit observed effects of the treatment. Toxicity and therapeutic efficacy of such compounds can be determined by standard pharmaceutical procedures in vitro (i.e., cell cultures) or in vivo (i.e., experimental animal models), e.g., for determining the $LD_{50}$ (the dose lethal to 50% of the population) and the $ED_{50}$ (the dose therapeutically effective in 50% of the population). The dose ratio between toxic and therapeutic effects is the therapeutic index (or therapeutic ratio), and can be expressed as the ratio $LD_{50}/ED_{50}$. Conjugates that exhibit therapeutic indices of at least 1, 1.5, 2, 3, 4, 5, 6, 7, 8, 9, 10, and 20 are described herein.

To facilitate a better understanding of the present disclosure, the following examples of certain aspects of some embodiments are given. In no way should the following examples be read to limit, or define, the entire scope of the invention.

Example 1

Materials and Methods

Materials.

Hyaluronic acid (HA), with an average molecular weight of 31 kD was purchased from Lifecore. Analytical grade acetonitrile and synthesis grade trifluoro acetic acid (TFA) were purchased from Fisher Scientific. Research grade sodium acetate, acetic acid, and $D_2O$ were purchased from Sigma. Water was provided by a Labconco Water PRO PS ultrapure water purification unit. Poly (DL-lactic-co-glycolic acid) (50:50) (PLGA; inherent viscosity of 1.05 dL/g, Mw ~101 kDa) was purchased from LACTEL Absorbable Polymers International (Pelham, Ala., USA). Pluronic® F68 (Mw ~8.4 kD) and Pluronic® F108 (Mw ~14.6 kD) were obtained from BASF Corporation. Acetone, diethyl ether and 1×Tris/EDTA buffer solution (pH 8) were obtained from Fisher Scientific. D-mannitol, Dess-Martin periodianine, tert-butyl carbazate (TBC), trinitrobenzenesulfonic acid (TNBS), dichloromethane anhydrous (DCM) and Triton X-100 were purchased from Sigma-Aldrich.

Peptide Synthesis.

Aminooxy peptides were synthesized using 9-fluorenylmethyloxycarbonyl-protected amino acid chemistry on polyethylene glycol-polystyrene resins. The peptides synthesized were aminooxy-LABL (aminooxy-ITDGEATDSG, Ao-LABL), a ligand of ICAM-1 (SEQ ID NO: 54) and aminooxy-PLP (aminooxy-HSLGKWLGHPDKF, Ao-PLP), an antigen derived from proteolipid protein amino acids 139-151 ($PLP_{137-151}$) (SEQ ID NO: 55). Peptides were deprotected, cleaved from resin, and isolated by precipitation in ether. Purification was completed using preparatory High Performance Liquid Chromatography (HPLC) followed by lyophilization. Peptide identity was verified and purity/content was assessed using Mass Spectroscopy and analytical HPLC. BPI, which is a fusion of PLP and LABL, was synthesized and purified as previously reported (HSLGKWLGHPDKF-AcGAcGAc-ITDGEATDSG) (SEQ ID NO: 56).

Reaction of Aminooxy Peptides to Polymers.

HA was dissolved in 20 mM Acetate buffer (pH 5.5±0.1 pH units) and aminooxy reactive peptide(s) added. When both LABL and PLP peptides were used, each was weighed separately, and then added simultaneously. After addition of the peptide(s), the reaction solution pH was adjusted back to pH 5.5±0.1 pH units. Reaction solutions were stirred at 500 RPM using magnetic stir bars for ~16 hr. After the reaction, the soluble antigen array (SAgA) product was purified by extensive dialysis to remove any unreacted peptide, and then lyophilized.

Gel Permeation Chromatography.

The relative molecular weight of the HA and of the SAgAs was estimated using a Viscotek GPC max VE 2001 GPC solvent/sample module, VE 3580 refractive index detector, and 270 Dual Detector with right angle light scattering. A tandem column setup of two Viscogel GMPWx1 columns (Viscotek) was used at a flow rate of 1 mL/min with isocratic elution in water for 30 min.

Conversion of Terminal Hydroxyl Groups to Terminal Aldehyde Groups on Pluronic® F108.

To conjugate peptides to Pluronic® on PLGA nanoparticles an oxidizing reagent was used to convert hydroxyl groups on Pluronic®F108 (Pluronic®F108-OH) to aldehyde groups (Pluronic®F108-CHO). One gram Pluronic®F108-OH was dissolved in 30 mL DCM. Subsequently, 58.1 mg Dess-Martin periodianine was added and reacted for 24 h at room temperature. The product was purified by precipitation in cold diethyl ether, followed by filtration. The obtained Pluronic®F108-CHO was verified by nuclear magnetic resonance spectroscopy ($^1$H-NMR). Deuterated chloroform ($CDCl_3$) was used to dissolve the samples. The conversion percentage was also determined. An excess amount of TBC was added to the Pluronic®F108-CHO solution as previously described and the amount of unreacted TBC was measured using TNBS solution. A UV/VIS Spectrophotometer (SpectraMax) operating at 334 nm was employed to quantify the colored mixture of TBC and TNBS.

Preparation of PLGA Nanoparticles.

A solvent displacement method was employed to prepare PLGA nanoparticles (NPs). Briefly, PLGA (inherent viscosity 1.05 dL/g) was dissolved in acetone (15 mg/mL). A mixture of 1425 μL of PLGA solution and 75 μL 1×Tris/EDTA buffer solution was injected into 15 mL water containing 0.1% w/v Pluronic® using a syringe pump (10 mL/hr) while stirring (1000 rpm). Stirring was continued for 1.5 hours and then excess surfactant was removed by centrifugation (15,000 rpm, 15 min, 4° C.) for 3 cycles, resuspending in water between cycles. Using a sonication bath (Branson 2510 ultrasonic cleaner). A 25:75 Pluronic® (CHO:OH) ratio was used for fabrication of NPs with conjugated PLP (NP-$Array_{PLP}$), LABL (NP-$Array_{LABL}$), or both (NP-$Array_{LABL-PLP}$). The 0:100 Pluronic® (CHO:OH) ratio was used as the control (NP-Blank) without any peptide conjugation.

Conjugation of Peptides to PLGA Nanoparticles.

Stock solutions of 2 mg/mL of PLP and LABL peptides were separately prepared. To prepare the NP-$Array_{PLP}$, 4.0 mL of PLP stock was added to 102.3 mg NPs in 3.52 mL of water. For NP-$Array_{LABL}$ preparation, 2.6 mL of LABL stock was added to 112.5 mg NPs in 3.2 mL of water. Finally, to prepare the NP-$Array_{LABL-PLP}$, 3.6 mL of PLP stock and 2.34 mL of LABL stock were added to 227.84 mg NPs in 2.844 mL water. The volume of each nanoparticle sample was increased to 50 mL using $ddH_2O$. The volume of NP-Blank sample was also increased up to 50 mL as well (227.84 mg NPs). The samples reacted overnight and were purified by centrifugation (15,000 rpm, 15 min, 4° C.) for 3 cycles, resuspending in water between cycles.

Dynamic Light Scattering.

Particle size was measured using a ZetaPALS dynamic light scattering instrument (Brookhaven Instrument Corporation).

High Performance Liquid Chromatography.

Quantification of free peptide post reaction was accomplished by gradient reversed phase HPLC (SHIMADZU) using a Vydac HPLC protein and peptide C18 column. HPLC system was composed of an SCL-20A SHIMADZU system controller, LC-10AT VP SHIMADZU liquid chromatograph, SIL-10A XL SHIMADZU auto-injector set at 75 μL injection volume, DGU-14A SHIMADZU degasser, sample cooler, and SPD-10A SHIMADZU UV-vis detector (220 nm). A personal computer equipped with SHIMADZU class VP software controlled the HPLC-UV system. Gradient elution was conducted at constant flow of 1 mL/min, from 100% A to 35% A (corresponding to 0% B to 65% B) over 50 min, followed by an isocratic elution at 75% B for 3 min. Mobile phase compositions were (A) acetonitrile-water (5:95) with 0.1% TFA and (B) acetonitrile-water (90:10, v/v) with 0.1% TFA. At the completion of each analysis, the cartridge was equilibrated at initial conditions at 1 mL/min flow rate for 5 min with A.

Calculation of Peptide Density on the Surface of NPs.

Peptide surface density was calculated by subtracting the amount of peptide recovered after conjugation from the amount of peptide added to the NP suspension. This value was then divided by the total surface area assuming a normal Gaussian particle size distribution and using a particle density of 1.34 g/cm$^3$. NP-Blank suspension was used as a negative control. PLP and LABL at molar ratios of 100:0, 50:50, and 0:100 were added to the NP-Blank and peptide adsorption was quantified as an additional control. Peptide adsorption to blank particles or plastic was negligible.

Induction of EAE and Therapeutic Study.

SJL/J (H-2s) female mice, 4-6 weeks old, were purchased from The Jackson Laboratory and housed under specified, pathogen-free conditions at The University of Kansas. All protocols involving live mice were approved by the Institutional Animal Care and Use Committee. Mice were immunized subcutaneously (s.c) with 200 mg of $PLP_{139-151}$ in a 0.2 mL emulsion composed of equal volumes of phosphate-buffered saline (PBS) and complete Freund's adjuvant (CFA) containing killed *Mycobacterium tuberculosis* strain H37RA (final concentration of 4 mg/mL; Difco). The $PLP_{139-151}$/CFA was administered to regions above the shoulders and the flanks (total of four sites; 50 μL at each injection site). In addition, 200 ng/100 μL of pertussis toxin (List Biological Laboratories Inc.) was injected intraperitoneally (i.p.) on the day of immunization (day 0) and 2 days post-immunization. The mice received s.c. injections of each sample, equivalent to 100 nMol PLP/100 μL, on days 4, 7, 10. All NP samples were sonicated to disperse NPs before injection. For HA samples and controls, 100 μL of each vehicle was injected. For NP vehicles, 400 μL solution was used to assure suspension stability. Disease progression was evaluated blindly by the same observer using clinical scoring as follows: 0, no clinical signs of the disease; 1, tail weakness or limp tail; 2, paraparesis (weakness or incomplete paralysis of one or two hind limbs); 3, paraplegia (complete paralysis of two hind limbs); 4, paraplegia with forelimb weakness or paralysis; and 5, moribund (mice were euthanized if they were found to be moribund). Body weight was also measured daily.

Statistical Analysis

Statistical differences were determined by comparing treated groups to the negative control (PBS) for clinical disease score and body weight. A one-way analysis of variance (ANOVA) followed by Fisher's least significant difference was applied to these data. All analyses were performed using GraphPad Software (GraphPad Software Inc.).

Results

Characterization of Polymeric Soluble Antigen Arrays.

Figure 1:
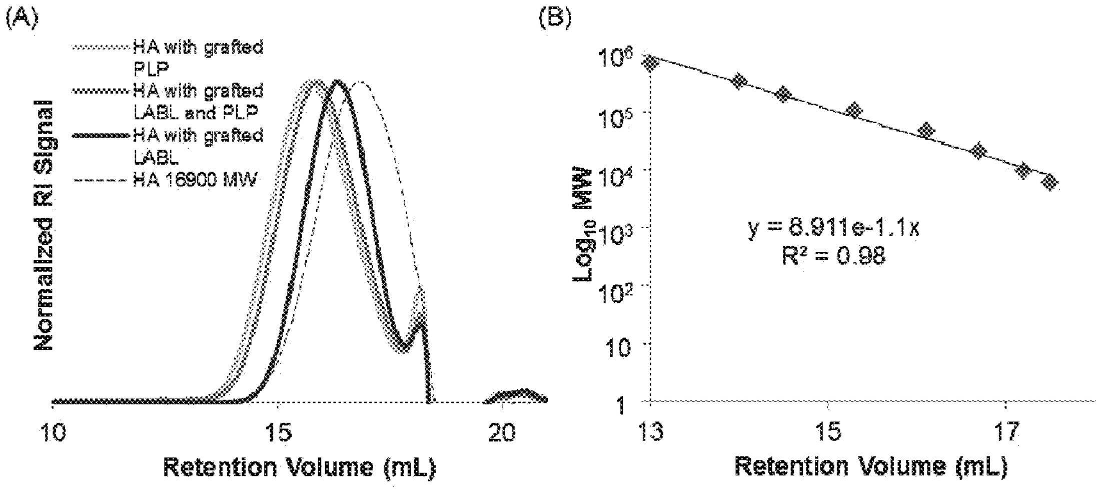
FIG. 1 shows (A) SEC analysis of HA grafted with a single peptide (PLP or LABL) or grafted with a 1:1 peptide mixture showed an increase in MW as compared to unmodified HA. (B) Calibration curve for pullulan standards used to calculate HA polymer graft conjugate product MW.
Figures 2A, 2B:
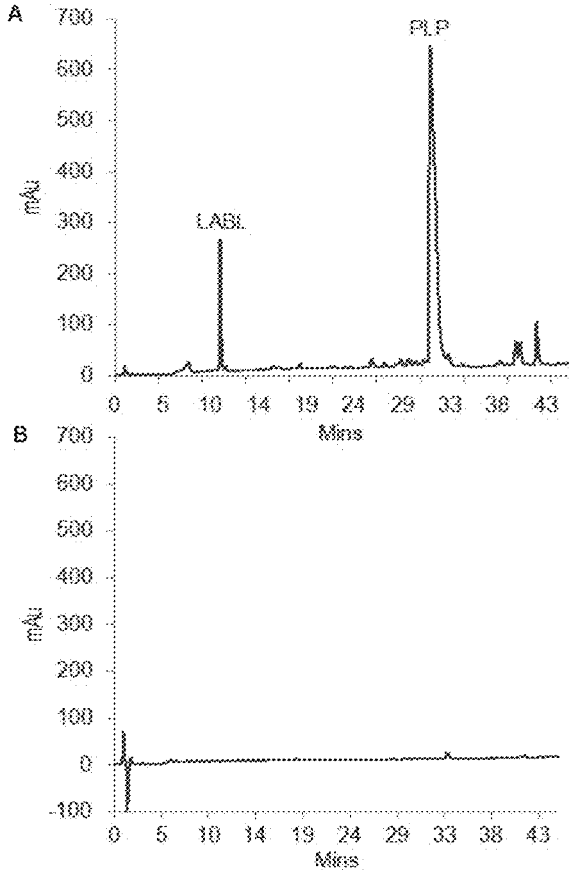
FIGS. 2A-2B are graphs depicting (A) an example HPLC chromatogram of peptides hydrolyzed from the conjugate product showing the presence of both the Ao-LABL and Ao-PLP peptides; and (B) HPLC chromatogram of dialysate showing the absence of both the Ao-LABL and Ao-PLP peptides suggesting nearly all peptide was reacted to HA.

Gel permeation chromatography (GPC) and HPLC were employed to observe any change in retention time resulting from the presence of peptides grafted to the HA. When analyzed by GPC, the product showed a decrease in retention time suggesting an increase in molecular weight relative to the HA (FIG. 1). To quantify the amount of peptide grafted to the polymer, the product retentate and dialysate (containing unreacted peptide) were analyzed by HPLC after extensive dialysis. The product retentate was incubated at room temperature in pH 2 mobile phase buffer. At this pH, the N-oxime bond is rapidly hydrolyzed, thus allowing quantification of the peptide released from the product. Typical chromatograms showed the presence of the Ao-LABL peptide, the Ao-PLP peptide, or both (FIG. 2A). The dialysate showed no peaks. Any unreacted peptide was below the limit of detection of the HPLC (FIG. 2B). A 1:1 ratio of the peptides was achieved. Any difference in peak intensities was primarily due to the different absorption coefficients of these peptides. Data for all the SAgA types suggested highly efficient grafting (Table 6).

TABLE 6

| Sample | LABL Conc (nMol) | PLP Conc (nMol) | Final Ratio |
|---|---|---|---|
| $SAgA_{LABL\text{-}PLP}$ | 325 | 275 | 1.2:1 |
| $SAgA_{LABL}$ | 462 | — | n/a |
| $SAgA_{PLP}$ | — | 286 | n/a |
| NP-$Array_{LABL\text{-}PLP}$ | 8.2 | 7.6 | 1.1:1 |
| NP-$Array_{LABL}$ | 16.0 | — | n/a |
| NP-$Array_{PLP}$ | — | 17.6 | n/a |

Conversion of Terminal Hydroxyl Groups to Terminal Aldehyde Groups on Pluronic® F108.

The hydroxyl groups of Pluronic® were converted to aldehyde groups in order to utilize Pluronic® for conjugation to the terminal aminooxy of the PLP and LABL peptides. Pluronic® F108-CHO with aldehyde groups were prepared by the Dess-Martin oxidation reaction. To confirm conversion, $^1$H NMR spectra from before and after the reaction were compared. After conversion, the signal corresponding to the aldehyde group (δ=9.75) appeared which confirmed the conversion of hydroxyl groups to aldehyde groups. The yield of the conversion was also determined to be 74.0% via a colormetric TBC/TNBS assay.

Characterization of NP-Arrays. Reversed phase HPLC was used to indirectly determine the amount of peptide conjugated to NPs. NPs were centrifuged from solution and the amount of unreacted peptide was quantified from the supernatant. Blank NPs and empty vials were used as controls to ensure that peptide was not being adsorbed to surfaces non-specifically. The peptide density on the surface of NPs was calculated based on the total NP surface area, assuming a normal Gaussian particle size distribution (Table 7). The NP-$Array_{LABL\text{-}PLP}$ had a 1.1:1 ratio of LABL:PLP peptide on the surface. Light scattering data showed that all NP-Arrays showed similar size both before and after peptides were conjugated to the surface (Table 7). For the nanoparticles displaying only one peptide, the NP-$Array_{PLP}$ had a similar surface density as the NP-$Array_{LABL}$ (Table 6). The difference was nest significant.

TABLE 7

| Sample ID | Pluronic ratio (F108-CHO:F68-OH) | Particle Size (nm)* After fabrication | |
|---|---|---|---|
| NP-$Array_{LABL\text{-}PLP}$ | 25:75 | 171 ± 7.2 | NP-$Array_{LABL\text{-}PLP}$ |
| NP-$Array_{LABL}$ | 25:75 | 171 ± 7.2 | NP-$Array_{LABL}$ |
| NP-$Array_{PLP}$ | 25:75 | 171 ± 7.2 | NP-$Array_{PLP}$ |
| NP-Blank | 0:100 | 158 ± 1.9 | NP-Blank |

Suppression of EAE by Arrays.

The SAgAs and NP-Arrays were evaluated in an EAE model induced in SJL/J mice. The in vivo study designs are outlined in Table 8.

TABLE 8

| Group | Dose (nMol PLP/100 μL) | Description |
|---|---|---|
| Study I: Initial Efficacy Study | | |
| Hyaluronic Acid | | Polymer control |
| $SAgA_{LABL\text{-}PLP}$ | 100 | LABL and PLP grafted to HA |
| PBS | 0 | Negative Control |
| Study II: Dose Ranging Study | | |
| $SAgA_{LABL\text{-}PLP}$ | 100 | Low Dose |
| $SAgA_{LABL\text{-}PLP}$ | 200 | Medium Dose |
| $SAgA_{LABL\text{-}PLP}$ | 400 | High Dose |
| PBS | 0 | Negative Control |
| BPI | 100 | Positive Control |
| Study III: Polyvalency vs. Scaffold | | |
| $SAgA_{LABL\text{-}PLP}$ | 200 | HA graft LABL and PLP |
| $SAgA_{LABL}$ | 200 nMol LABL | HA graft LABL |
| $SAgA_{PLP}$ | 200 | HA graft PLP |
| NP-$Array_{LABL\text{-}PLP}$ | 100 | Nanoparticle graft LABL and PLP |
| NP-$Array_{LABL}$ | 100 | Nanoparticle graft LABL |
| NP-$Array_{PLP}$ | 100 | Nanoparticle graft PLP |
| PBS | 0 | Negative Control |
| BPI | 100 | Positive Control |

The disease onset usually occurs around day 8 and progresses to remission around day 20. Eight-12 days after immunization, the mice showed disease signs, such as weakness, paralysis of their tail and limbs, and loss of body weight. Subcutaneous injections of each sample were given on days 4, 7, 10. $SAgA_{LABL\text{-}PLP}$ inhibited the progression of EAE more effectively ($p<0.05$, day 17) than the 28 kDa HA which was used as the SAgA backbone (FIG. 3). The mice in the $SAgA_{LABL\text{-}PLP}$ treatment group had very low clinical scores throughout the study (FIG. 3A) and scores were significantly lower (at the peak of the disease; days 11-17) than those of groups treated with PBS. The mice treated with $SAgA_{LABL\text{-}PLP}$ also had significantly better maintenance of body weight (FIG. 3B) compared to the negative control PBS group (days 12-17). In addition, 50% of the mice receiving the $SAgA_{LABL\text{-}PLP}$ treatment never developed EAE during the course of study. Mice that did not show symptoms exhibited a delay in disease onset (FIG. 3C). HA was dosed at a concentration equal to the molar concentration of HA in the dosed $SAgA_{LABL\text{-}PLP}$. Previously, a similar molecular weight of HA was shown to suppress disease by activating toll-like receptors or increasing $T_H2$ response, thus some therapeutic efficacy was expected for HA. Treatment with $SAgA_{LABL\text{-}PLP}$ showed suppression of EAE relative to the HA polymer as well.

Once the efficacy of the $SAgA_{LABL\text{-}PLP}$ was confirmed, the effect of $SAgA_{LABL\text{-}PLP}$ dose was evaluated and compared to the positive control PLP-BPI. The BPI molecule was composed of three portions: the EAE antigen peptide (PLP) and the ICAM-1 inhibitor (LABL) separated by a spacer (see methods). Clinical results for BPI were consistent with previously published data. The effect of $SAgA_{LABL\text{-}PLP}$ dose was evaluated by increasing the concentration to 200 nM and 400 nM as defined by the molar quantity of PLP antigen administered. Clinical scores suggested that increasing the $SAgA_{LABL\text{-}PLP}$ dose to 200 nM PLP reduced disease score ($p<0.05$, day 15, FIG. 4A). Further increasing the concentration to 400 nM PLP gave results similar to the 200 nM dose as no significant difference was seen between dose levels. These results were corroborated by the weight loss in each treatment group, which showed similar trending (FIG. 4B).

The role of scaffold was investigating by replacing the hyaluronic acid polymer backbone with a PLGA-Pluronic® nanoparticle. The LABL and PLP peptides were grafted to the nanoparticles by reacting the aminooxy peptides to the particle surface. These particles were then delivered as a suspension with the dose of PLP at 100 nMol. The clinical scoring results showed both the soluble polymer $SAgA_{LABL\text{-}PLP}$ and colloidal NP-$Array_{LABL\text{-}PLP}$ provided disease suppression (FIG. 5A), however, the NP-$Array_{LABL\text{-}PLP}$ had a quicker onset and high incidence of disease when compared to the $SAgA_{LABL\text{-}PLP}$ (FIG. 5C). Animal weight data indicated that the $SAgA_{LABL\text{-}PLP}$ and NP-$Array_{LABL\text{-}PLP}$ maintained animal body weight similarly throughout the study (FIG. 5B).

The effect of multivalent display of only antigen or only the cell-adhesion inhibitor was also investigated by conjugating either PLP peptide or LABL targeting peptide to the HA polymer or to the NPs. As an additional control a mix of free LABL and PLP peptides was tested. Clinical scores suggested that the multivalent LABL treatments ($SAgA_{LABL}$ and NP-$Array_{LABL}$) exacerbated disease with data trending higher than that of the PBS control. Conversely, the multivalent PLP treatments ($SAgA_{PLP}$ and NP-$Array_{PLP}$) showed trending similar to or slightly lower than the PBS control (FIG. 6A). Statistical analysis of these results, however, did not demonstrate statistical significance for either treatment. The weight loss results corroborated scoring data for both the multivalent LABL and multivalent PLP treatments (FIG. 6B). The data for the mixture of free peptides matched the PBS control indicating no clinical benefit (FIG. 7). An outline of all results and statistical significance compared to negative PBS control are summarized in Table 9.

TABLE 9

| Treatment Group | PLP conc. (nMol) | MW (Daltons) | Clinical Data Significance compared to PBS: Score | % Weight loss | Comments |
|---|---|---|---|---|---|
| 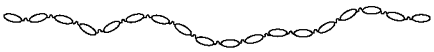 Hyaluronic Acid Alone | 4.5 mg/mL** | 28000 | Days 11-14, $p < 0.01$ | Days 11-14, $p < 0.01$ | HA is a natural CD40 antagonist and provides minimal protection |
| 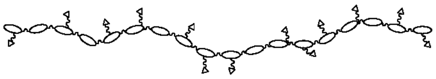 $SAgA_{LABL}$ | 100* | ~70000 | None | None | Grafting targeting moiety only causes disease exacerbation |
| 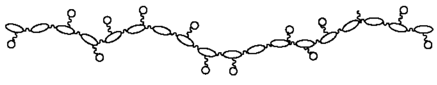 $SAgA_{PLP}$ | 100 | ~80000 | None | None | Grafting antigen showed non-significant suppression |
| 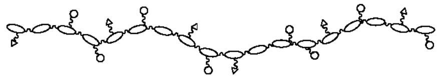 $SAgA_{LABL\text{-}PLP}$ | 100 | ~80000 | Days 11-17, $p < 0.01$ | Days 12-17, $p < 0.05$ | 200 nMol may be optimal dose for $SAgA_{LABL\text{-}PLP}$ |
| | 200 | ~80000 | Days 11-15, $p < 0.01$ | Days 11-15, $p < 0.01$ | |
| | 400 | ~80000 | Days 12-14, $p < 0.01$ | Days 12-14, $p < 0.05$ | |
| | 200 | ~50000 | Days 11-17, $p < 0.001$ | Days 11-17, $p < 0.01$ | Decreased size provides delayed disease onset and decreased duration |

TABLE 9-continued

| | PLP | | Clinical Data Significance compared to PBS | | |
|---|---|---|---|---|---|
| Treatment Group | conc. (nMol) | MW (Daltons) | Score | % Weight loss | Comments |
| 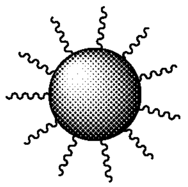 Blank NP | 100* | n/a | None | None | Nanoparticle based SAgA do not provide suppression of EAE |
| 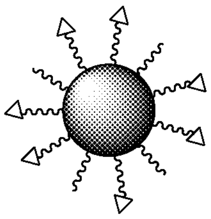 NP-Array$_{LABL}$ | 100 | n/a | Day 12, $p < 0.001$ | None | |
| 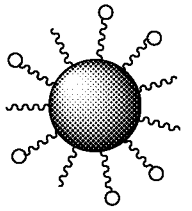 NP-Array$_{PLP}$ | 100 | n/a | Day 12, $p < 0.001$ | Day 12, $p < 0.001$ | |
| 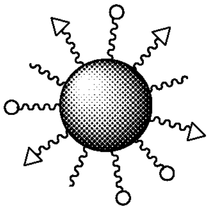 NP-Array$_{LABL-PLP}$ | 100 | n/a | Day 12, $p < 0.001$ | Days 12-16, 18-22, $p < 0.01$ | |

Example 2

Materials and Methods

Materials.

Hyaluronic acid (HA), with an average molecular weight of 17 and 31 kDa were purchased from Lifecore. Analytical grade acetonitrile, synthesis grade trifluoro acetic acid (TFA), and PBS buffer were purchased from Fisher Scientific. Research grade sodium acetate, acetic acid, and $D_2O$ and heparin were purchased from Sigma. Water was provided by a Labconco Water PRO PS ultrapure water purification unit.

Mice.

Four-6 weeks old SJL/J (H-2s) female mice were purchased from The Jackson Laboratory. Animals were housed under specified pathogen-free conditions at The University of Kansas Animal Care Facility. The University of Kansas Institutional Animal Care and Use Committee approved all protocols involving live mice.

Peptide Synthesis.

9-fluorenylmethyloxycarbonyl-protected amino acid chemistry on polyethylene glycol-polystyrene resins was used to synthesize the aminooxy peptides. Peptides synthesized for this study were aminooxy-LABL (aminooxy-ITDGEATDSG, Ao-LABL), a ligand of ICAM-1 (SEQ ID NO: 54), aminooxy-IBR (aminooxy-GGGPRGGVS, Ao-IBR), a ligand of LFA-1 (SEQ ID NO: 57), and aminooxy-PLP (aminooxy-HSLGKWLGHPDKF, Ao-PLP) (SEQ ID NO: 55), an antigen derived from proteolipid protein amino acids 139-151 ($PLP_{137-151}$). Each peptide was deprotected, cleaved from resin, and isolated by precipitation in ether. Preparatory High Performance Liquid Chromatography (HPLC) was employed to purify the peptides, followed by lyophilization. Purity/content and peptide identity were verified using analytical HPLC and Mass Spectroscopy. PLP-BPI, a fusion of PLP and LABL (HSLGKWLGHPDKF- AcGAcGAc-ITDGEATDSG) (SEQ ID NO: 56), was synthesized and purified as previously reported.

Reaction of Aminooxy Peptides to Polymers.

The HA scaffolds were dissolved into 20 mM Acetate buffer (pH 5.5±0.1 pH units) and aminooxy reactive peptide(s) added. When multiple peptide species were used, each was weighed separately, and then both peptides were added simultaneously. Reaction solution pH was adjusted back to pH 5.5±0.1 pH units after addition of the peptide(s). Reaction solutions were stirred at for ~16 hr. After the reaction, the soluble antigen array (SAgA) product was purified by extensive dialysis to remove any unreacted peptide, and then lyophilized.

High Performance Liquid Chromatography.

Reversed phase HPLC (SHIMADZU) using a Vydac HPLC protein and peptide C18 column was used to quantified conjugated peptide. The HPLC system was made up of an SCL-20A SHIMADZU system controller, LC-10AT VP SHIMADZU liquid chromatograph, SIL-10A XL SHIMADZU auto-injector set at 75 μL injection volume, DGU-14A SHIMADZU degasser, sample cooler, and SPD-10A SHIMADZU UV-vis detector (220 nm). The HPLC-UV system was controlled by a personal computer equipped with SHIMADZU class VP software. A gradient elution was conducted at constant flow of 1 mL/min, from 100% A to 35% A (corresponding to 0% B to 65% B) over 50 min, followed by an isocratic elution at 75% B for 3 min. The mobile phases were (A) acetonitrile-water (5:95) with 0.1% TFA and (B) acetonitrile-water (90:10, v/v) with 0.1% TFA. After each analysis, the cartridge was equilibrated at initial conditions at 1 mL/min flow rate for 5 min with A.

Preparation of Near Infrared Dye IR-820.

To prepare the dye, 125 mg 6-aminocaproic acid was dissolved in dry DMF (20 mL). TEA (130 μL) was added and the mixture was allowed to stir under argon for ~5 min. Then, 500 mg IR-820 was added. A reflux condenser was attached and the mixture was heated to 85° C. for 3 hr in the dark. After the reaction the solvent was removed using a rotovap and placed under vacuum over night to dry.

Conjugation of IR-820 to Hyaluronic Acid.

IR-820-5 aminohexanoic acid dye was dissolved into water. EDC was added and the solution pH was adjusted to 4.5. Then, DMAP was added and the solution was stirred, in the dark, for 5 min. After activation of IR-820 (5 min), hyaluronic acid was added to the flask and the solution was stirred in the dark, for 48 hours. The product was purified by dialyzing against 95% EtOH for 8 hours, then against water twice (8 Hours a time) in the dark. The retentate was lyophilized and the dye content of the product was confirmed using NMR.

Nuclear Magnetic Resonance Spectroscopy.

For dye content analysis, samples were dissolved in $D_2O$ to a concentration of 10 mg/mL. H1 spectra were acquired on a Bruker 400 MHz spectrometer at 25° C.

Induction of EAE and Therapeutic Study.

Four-6 week-old SJL/J female mice were immunized subcutaneously (s.c) with 200 mg of $PLP_{139-151}$ in a 0.2 mL emulsion composed of equal volumes of complete Freund's adjuvant (CFA) containing killed *Mycobacterium tuberculosis* strain H37RA (final concentration of 4 mg/mL; Difco) and phosphate-buffered saline (PBS) containing PLP. The $PLP_{139-151}$/CFA emulsion was administered to regions above the shoulders and the flanks (total of four sites; 50 μL at each injection site). Additionally, 200 ng/100 μL of pertussis toxin (List Biological Laboratories Inc.) was injected intraperitoneally (i.p.) on the day of immunization (day 0) and 2 days post-immunization. Mice received s.c. injections of each sample, equivalent to 200 nMol PLP/100 μL, on days 4, 7, 10. One hundred μL of each vehicle was injected for all samples and controls. Disease progression was evaluated blindly by the same observer using clinical scoring as follows: 0, no clinical signs of the disease; 1, tail weakness or limp tail; 2, paraparesis (weakness or incomplete paralysis of one or two hind limbs); 3, paraplegia (complete paralysis of two hind limbs); 4, paraplegia with forelimb weakness or paralysis; and 5, moribund (mice were euthanized if they were found to be moribund). Body weight was also measured daily.

Cytokine Analysis.

Blood samples were taken from each mouse via mandibular bleeds (~100 uL) on days 0, 6, 12, 18, 25. To ensure there was enough sample to perform ELISA cytokine testing blood from, two mice within the same group was pooled at each time point for a total of four samples per group. Samples were collected in heparin-containing tubes and centrifuged to separate red blood cells. Plasma was collected and sent for cytokine analysis to the Cytokine Core Laboratory at the University of Maryland. The cytokines analyzed were IL-2, IL-4, IL-10, IL-17, TNF-α, and TGF-β.

In Vivo Imaging.

In vivo imaging was completed using the Maestro Imaging Suite. Animals were anesthetized using an isoflurane vaporizer and IR-820 labeled SAgA was injected s.c. at the base of the neck. After injection images were taken of the animal's top, left, bottom, and right side by rotating the animal in the exposure pane. The animal was imaged at defined time points over a 24 hour period to track the drainage and clearance of the SAgA from the injection site.

Statistical Analysis.

Statistical differences were determined by comparing treated groups to the negative control (PBS) for clinical disease score and body weight. A one-way analysis of variance (ANOVA) followed by Fisher's least significant difference was applied to these data. For individual clinical day scores and cytokine measurements T test was employed. All analyses were performed using GraphPad Software (GraphPad Software Inc.).

Results

Characterization of Polymeric Soluble Antigen Arrays.

The concentration of peptide grafted to the HA backbone was quantified by HPLC. (Table 10) Peptide was released from scaffold by incubating the SAgA product in pH 2 mobile phase buffer at room temperature. Chromatograph results demonstrated the presence of the Ao-LABL or Ao-IBR peptide, and the Ao-PLP peptide at approximately the desired 1:1 ratio for all products. All SAgA results showed a high level of conjugation efficiency, >90%.

TABLE 10

| Sample | LABL/IBR Conc. (nMol) | PLP Conc. (nMol) | Final Ratio |
|---|---|---|---|
| 50 kDa $SAgA_{LABL-PLP}$ | 475 | 300 | 1.5:1 |
| 80 kDa $SAgA_{LABL-PLP}$ | 396 | 283 | 1.4:1 |
| 50 kDa $SAgA_{IBR-PLP}$ | 297 | 377 | 1:1.3 |
| 80 kDa $SAgA_{IBR-PLP}$ | 262 | 334 | 1:1.3 |

Efficacy of SAgAs was evaluated in the EAE model induced in SJL/J mice. The study design is outlined in Table 11 below. Typically disease onset occurs at approximately day 8 and progresses to remission around day 20. Disease is manifested by physical signs, such as weakness, paralysis of their tail and limbs, and loss of body weight. Injections of each sample were given subcutaneously on days 4, 7, 10.

TABLE 11

| Study I: Initial Efficacy Study | | | | | |
|---|---|---|---|---|---|
| | PLP conc. | Mw | Clinical Significance vs PBS | | |
| Group | (nMol) | (Dal) | Score | % Weight loss | Comments |
| 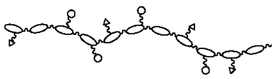 50 kDa $SAgA_{LABL-PLP}$ | 100 | ~50000 | $p < 0.05$, Days 14 & 17 | n/a | |
| 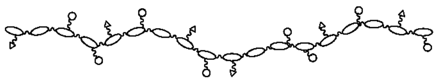 80 kDa $SAgA_{LABL-PLP}$ | 200 | ~80000 | $p < 0.05$, Days 14, 17-19 | $p < 0.05$, Days 15-21 | |
| 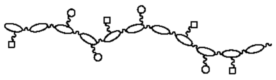 50 kDa $SAgA_{IBR-PLP}$ | 400 | ~50000 | $p < 0.05$, Days 14, 17-19 | $p < 0.05$, Days 19 | |
| 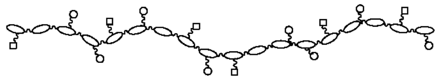 80 kDa $SAgA_{IBR-PLP}$ | 200 | ~80000 | $p < 0.05$, Days 14, 17-19 | $p < 0.05$, Days 18 | |
|  PLP-BPI | 100 | ~3000 | $p < 0.05$, Days 14 & 17 | $p < 0.05$, Days 16 | Positive Control |
| PBS | 0 | n/a | n/a | n/a | Negative Control |

Effect of Cell Adhesion Target on Suppression.

SAgAs targeting either ICAM-1 ($SAgA_{LABL-PLP}$) or LFA-1 ($SAgA_{IBR-PLP}$) performed significantly better than the negative PBS control in clinical score (p<0.01, for days 14 & 17-19 for both) (FIG. 8A). Additionally, the mice treated with the targeted SAgAs also had significantly better maintenance of body weight (p<0.05, for days 15-21 for $SAgA_{LABL-PLP}$ and day 18 for $SAgA_{IBR-PLP}$) compared to the negative control PBS group (FIG. 8B). Of all the treated groups, only the $SAgA_{IBR-PLP}$ had mice that never developed EAE as identified by a clinical score of ≥1 (FIG. 8C). This data compared well to the positive control PLP-BPI and no statistical difference was seen between treatments with SAgAs vs. the positive control.

Effect of SAgA Size on Suppression.

Both the 50 kDa and 80 kDa $SAgA_{LABL-PLP}$ and the 50 kDa and 80 kDa $SAgA_{IBR-PLP}$ inhibited the disease progression of EAE as evidenced by very low clinical scores. This treatment was more effectively than the negative PBS control (FIG. 9A). Clinical suppression was significantly improved over PBS treatment for the 50 kDa and 80 kDa $SAgA_{LABL-PLP}$ (p<0.05, for days 14 & 17 and 14 & 17-19 respectively) as well as the 50 kDa and 80 kDa $SAgA_{IBR-PLP}$ (p<0.05, for days 14 & 17-19 for both). The treated mice also had better maintenance of body weight (FIG. 9B) compared to the negative control PBS group for all tested groups. Complete statistics are outlined in Table 10. Additionally, the smaller 50 kDa $SAgA_{IBR-PLP}$ delayed the onset of disease better than the 80 kDa $SAgA_{IBR-PLP}$ (p<0.05, day 11) with incidence of disease occurring two days later with the 50 kDa $SAgA_{IBR-PLP}$. A high percentage of animals treated with the 50 kDa $SAgA_{IBR-PLP}$ never developed clinical scores ≥1 (FIG. 9C). This data compared well to the positive control PLP-BPI and no statistical difference was seen between treatments with SAgAs vs. the positive control.

In Vivo Imaging of SAgAs.

Both the 50 and 80 kDa $SAgA_{LABL-PLP}$ were imaged and compared to a 30 kDa HA (the 80 kDa backbone) and a 70 kDa HA that was similar in Mw to the final products. After injection of the IR820-labeled HA or $SAgA_{LABL-PLP}$, the drainage from the injection site was tracked and images were acquired over 24 hours (FIG. 10). The 30 kDa HA (FIG. 10A) appeared to drain from the injection site, and was cleared by 1440 min. The 70 kDa HA (FIG. 10B) showed a relatively shorter drainage time with the labeled HA detectable only until 500 min. For the labeled SAgA conjugates, the drainage time more closely resembled that of the smaller 30 kDa HA rather than the 70 kDa HA. The 50 kDa $SAgA_{LABL-PLP}$ (FIG. 10C) showed drainage from the injection site. Clearance was not achieved until 1440 min, similar to the 30 kDa HA. The larger 80 kDa $SAgA_{LABL-PLP}$ (FIG. 10D) showed similar drainage, but it was still visible even after 1260 minutes. While these results are qualitative, they do provide some insight into the location of the SAgA conjugates at different time points.

Effect of SAgA on Cytokine Profile.

The plasma samples were analyzed for 6 cytokines; IL-2, IL-4, IL-10, IL-17, TNF-α, and IFN-γ. Baseline levels of each cytokines were measured at Day 0 before disease induction. IL-2 and IL-10 were below the limit of detection in all samples. Examination of IL-4, IL-17, TNF-α, and IFN-γ all showed that treatment with SAgAs led to differences in the cytokine production profiles when compared to both the PBS and PLP-BPI controls. The largest differences were seen with the levels of IFN-γ, TNF-α, and IL-17 data, while smaller differences were seen with IL-4 levels (FIG. 11). While mice receiving PBS had very high average concentrations of IFN-γ by day 6 (72 pg/mL), however, the treatment groups suppressed IFN-γ production. The PLP-BPI (31 pg/mL) and the 50 kDa $SAgA_{IBR-PLP}$ (38 pg/mL) treatments provided moderate suppression with an average of ~40% reduction in peak expression of IFN-γ on Day 6. The lowest IFN-γ levels were seen with both the 50 and 80 kDa $SAgA_{LABL-PLP}$ (12 and 14 pg/mL respectively) and the 80 kD $SAgA_{IBR-PLP}$ (6 pg/mL), correlating to an ~80-90% reduction compared to the PBS controls.

For both TNF-α and IL-17, treatment with all groups led to an increase in the circulating cytokine concentrations compared to the PBS control. Similar to the IFN-γ data, peak concentrations of TNF-α occurred on day 6 for the PBS samples; however, these levels were very low at 1.8 pg/mL. The PLP-BPI reached 3.1 pg/mL of TNF-α on day 6. The 50 kDa $SAgA_{LABL-PLP}$ (3.7 pg/mL), 80 kDa $SAgA_{LABL-PLP}$ (3.4 pg/mL), and 80 kDa $SAgA_{IBR-PLP}$ (2.6 pg/mL) reached peak levels on day six. The 50 kDa $SAgA_{IBR-PLP}$ showed peak concentrations at days 6 and 18 (3.7 & 4.2 pg/mL).

The IL-17 data for the PBS control showed a peak concentration at day 6 (23 pg/mL). The 80 kDa $SAgA_{IBR-PLP}$ (45 pg/mL) and the PLP-BPI (40 pg/mL) control gave slightly elevated levels of IL-17; however, the PLP-BPI maintained these levels through day 12 (31 pg/mL), then returned toward baseline. Interestingly, peak concentrations at both days 6 and 18 were seen for the 50 kDa $SAgA_{IBR-PLP}$ (45 & 82 pg/mL), and both the 50 kDa $SAgA_{LABL-PLP}$ (66 & 21 pg/mL) and 80 kDa $SAgA_{LABL-PLP}$ (45 & 41 pg/mL).

Finally, IL-4 concentrations, though low, showed similar results for all samples (0.25-0.35 pg/mL), except for the 50 kDa $SAgA_{LABL-PLP}$ and 80 kDa $SAgA_{IBR-PLP}$, which had increased baseline levels. The 50 kDa $SAgA_{LABL-PLP}$ IL-4 levels decreased to day 6 levels similar to all other samples (0.25 pg/mL), however, increased at day 12 (1.1 pg/mL). The 80 kDa $SAgA_{IBR-PLP}$ level decreased to day 6 concentrations of 0.73 pg/mL. After day 6, the 80 kDa $SAgA_{IBR-PLP}$ IL-4 level continued to decrease, however, became elevated at the study end (0.2 pg/mL).

Example 3

Materials and Methods

Materials.

Hyaluronic acid (HA), with an average molecular weight of 17 and 31 kDa were purchased from Lifecore. Analytical grade acetonitrile, synthesis grade trifluoro acetic acid (TFA), and PBS buffer were purchased from Fisher Scientific. Research grade sodium acetate, acetic acid, and $D_2O$ and heparin were purchased from Sigma. Water was provided by a Labconco Water PRO PS ultrapure water purification unit.

Mice.

Four-6 weeks old SJL/J (H-2s) female mice were purchased from The Jackson Laboratory. Animals were housed under specified pathogen-free conditions at The University of Kansas Animal Care Facility. The University of Kansas Institutional Animal Care and Use Committee approved all protocols involving live mice.

Peptide Synthesis.

9-fluorenylmethyloxycarbonyl-protected amino acid chemistry on polyethylene glycol-polystyrene resins was used to synthesize the aminooxy peptides. Peptides synthesized for this study were aminooxy-LABL (aminooxy-ITDGEATDSG, Ao-LABL), a ligand of ICAM-1 (SEQ ID NO: 54), aminooxy-B7AP (aminooxy-EFMYPPPYLD, Ao-B7AP), a ligand of B7 (SEQ ID NO: 58), aminooxy-CAP1 (aminooxy MQPPGC, Ao-CAP1), a ligand of CD80 (SEQ ID NO. 59), aminooxy-SF2 (aminooxy-TEA-GAAGCRGVGVAFIGSCVFG-OH, a CTLA-4 ligand) (SEQ ID NO: 60), aminooxy-IBR (aminooxy-GGGPRGGVS, Ao-IBR) (SEQ ID NO: 57), aminooxy-MOG (aminooxy-GWYRSPFSRVVHL-OH), an antigen (SEQ ID NO: 61), and aminooxy-PLP (aminooxy-HSLGKWLGHPDKF, Ao-PLP), an antigen derived from proteolipid protein amino acids 139-151 ($PLP_{137-151}$) (SEQ ID NO: 55). Each peptide was deprotected, cleaved from resin, and isolated by precipitation in ether. Preparatory High Performance Liquid Chromatography (HPLC) was employed to purify the peptides, followed by lyophilization. Purity/content and peptide identity were verified using analytical HPLC and Mass Spectroscopy. PLP-BPI, a fusion of PLP and LABL (HSLGKWLGHPDKF-AcGAcGAc-ITDGEATDSG) (SEQ ID NO: 56), was synthesized and purified as previously reported.

Reaction of Aminooxy Peptides to Polymers.

The HA scaffolds were dissolved into 20 mM Acetate buffer (pH 5.5±0.1 pH units) and aminooxy reactive peptide(s) added. A 2 mg/mL solution of HA was used. When multiple peptide species were used, each was weighed separately, and then both peptides were added simultaneously. Reaction solution pH was adjusted back to pH 5.5±0.1 pH units after addition of the peptide(s). Reaction solutions were stirred at for ~24 hr at about 400 rpm. After the reaction, the soluble antigen array (SAgA) product was purified by extensive dialysis to remove any unreacted peptide. Dialysis was performed using 6000-8000 MWCO dialysis tubing. The dialysis wash should be 100× the reaction volume. Dialysis was performed for 24 hours changing dialysis solution at least three times. Following dialysis, the soluble antigen array (SAgA) product was then lyophilized.

High Performance Liquid Chromatography.

Reversed phase HPLC (SHIMADZU) using a Vydac HPLC protein and peptide C18 column was used to quantified conjugated peptide. The HPLC system was made up of an SCL-20A SHIMADZU system controller, LC-10AT VP SHIMADZU liquid chromatograph, SIL-10A XL SHIMADZU auto-injector set at 75 μL injection volume, DGU-14A SHIMADZU degasser, sample cooler, and SPD-10A SHIMADZU UV-vis detector (220 nm). The HPLC-UV system was controlled by a personal computer equipped with SHIMADZU class VP software. A gradient elution was conducted at constant flow of 1 mL/min, from 100% A to 35% A (corresponding to 0% B to 65% B) over 50 min, followed by an isocratic elution at 75% B for 3 min. The mobile phases were (A) acetonitrile-water (5:95) with 0.1% TFA and (B) acetonitrile-water (90:10, v/v) with 0.1% TFA. After each analysis, the cartridge was equilibrated at initial conditions at 1 mL/min flow rate for 5 min with A.

Induction of EAE and Therapeutic Study.

Four-6 week-old SJL/J female mice were immunized subcutaneously (s.c) with 200 mg of $PLP_{139-151}$ in a 0.2 mL emulsion composed of equal volumes of complete Freund's adjuvant (CFA) containing killed *Mycobacterium tuberculosis* strain H37RA (final concentration of 4 mg/mL; Difco) and phosphate-buffered saline (PBS) containing PLP. The $PLP_{139-151}$/CFA emulsion was administered to regions above the shoulders and the flanks (total of four sites; 50 μL at each injection site). Additionally, 200 ng/100 μL of pertussis toxin (List Biological Laboratories Inc.) was injected intraperitoneally (i.p.) on the day of immunization (day 0) and 2 days post-immunization. Mice received s.c. injections of each sample, equivalent to 200 nMol PLP/100 μL, on days 4, 7, 10. One hundred μL of each vehicle was injected for all samples and controls. Disease progression was evaluated blindly by the same observer using clinical scoring as follows: 0, no clinical signs of the disease; 1, tail weakness or limp tail; 2, paraparesis (weakness or incomplete paralysis of one or two hind limbs); 3, paraplegia (complete paralysis of two hind limbs); 4, paraplegia with forelimb weakness or paralysis; and 5, moribund (mice were euthanized if they were found to be moribund). Body weight was also measured daily.

Statistical Analysis.

Statistical differences were determined by comparing treated groups to the negative control (PBS) for clinical disease score and body weight. A one-way analysis of variance (ANOVA) followed by Fisher's least significant difference was applied to these data. For individual clinical day scores and cytokine measurements T test was employed. All analyses were performed using GraphPad Software (GraphPad Software Inc.).

Results

The results of the study indicate that 5 different signal-2 peptides give significant suppression of EAE as compared to PBS control. LABL-PLP, B7AP-PLP, and SF2-PLP SagAs showed significant suppression ($p<0.05$) as compared to control on days 11-15. CAP1-PLP showed significant suppression as compared to control on days 11-16. (FIG. 12). FIG. 13 shows % weight change of the mice over time. The data indicates significant weight maintenance ($P<0.05$) for all treatments as compared to controls on days 12-20. Table 12 below shows the HPLC results of manufactured SAgAs and corresponding number of peptides per 16900 Da HA polymer.

TABLE 12

| Conjugate | PLP Peptide Conc (mg/mL) | # PLP | Signal 2 peptide conc (mg/mL) | # Signal-2 Peptide |
|---|---|---|---|---|
| LABL, PLP SagA | 0.4347 | 8 | 0.3564 | 9 |
| B7AP, PLP SagA | 0.5605 | 14 | 0.3374 | 7 |
| CAP1, PLP SAgA #1 | 0.5007 | 11 | 0.0993 | 2 |
| SF2, PLP SagA #1 | 0.2191 | 3 | 0.2591 | 3 |
| CAP1, PLP* SAgA #2 | 0.3636 | 6 | 0.20531553 | 5 |
| SF2, PLP* SagA #2 | 0.1835 | 2 | 0.1237 | 1 |

FIG. 14 shows cross reactivity of MOG in PLP EAE scores. Score results showed significant suppression of PLP induced EAE using MOG-PLP SagA (Day 14) as compared to PBS control. LABL-PLP SagA showed significant suppression as compared to the controls on days 11-16. However, no significant weight maintenance of MOG SagAs in PLP EAE model as compared to PBS (FIG. 15). There was significant weight maintenance for LABL-PLP SAgA as compared to PBS on Days 11-15.

Mixtures of peptides combined, but not present on the same polymer, had a similar suppressive effect to peptides present on the same polymer were also considered. FIG. 16 shows the results of that study. Significant suppression of EAD occurred with a mixture of LABL-SagA and PLP-SagA as compared to PBS on days 11-15. FIG. 17 shows the percent weight change over time for SagA-PLP and SagA LABL mixtures as compared to controls and peptides present on the same polymer. Weight data showed significant weight maintenance ($P<0.05$) for LABL-SAgA and PLP-SAgA as compared to PBS on days 11-15.

The suppressive effect of mixtures of HA, PLP, and LABL and HA along were also compared to LABL-PLP SAgAs. Significant suppression of EAE with LABL-PLP SAgAs vs. polymer only (HA) occurred on days 11-14. Significant suppression of EAE with a physical mixture of polymer and peptide (HA, PLP, LABL mixed) on days 13-14 as compared to polymer only. (FIG. 18). FIG. 19 shows the % weight change in mice with specific mixtures of peptides or peptides on the same polymer as compared to HA alone and PBS. Significant weight maintenance ($P<0.05$) was seen for LABL-PLP SAgA treatment as compared to all controls on days 12-20.

Example 4

Method

Rapamycin, an immunosuppressant, was conjugated to HA and its suppressive effect was assessed. Rapamycin was reacted with succinic anhydride in toluene at 45° C. for 36h in the presence of novozyme 435 to get a first product. After purification, the first product was reacted with HA for 20 h, followed by dialysis. Conjugation percentage of rapamycin to HA was approximately 10 wt %. Similar animal studies were performed as described above in the previous examples.

Significant suppression ($P<0.05$) of EAE occurred with LABL-PLP SAgAs (days 12-18, and 20) and with Rapa-SAgA+PLP SAgA mixture (days 12-21, and 23) vs. PBS control. (FIG. 20). Weight data showed significant weight maintenance ($P<0.05$) for LABL-PLP SAgA (Days 12-18) and Rapa-SAgA+PLP SAgA mixture (days 12-21) treatments as compared to PBS Control.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

REFERENCES

Aharoni, R., D. Teitelbaum, et al. (2000). "Specific Th2 cells accumulate in the central nervous system of mice protected against experimental autoimmune encephalomyelitis by copolymer 1." Proc Natl Acad Sci USA 97(21): 11472-11477.

Ahmed, N. and S. Gottschalk (2009). "How to design effective vaccines: lessons from an old success story." Expert Rev Vaccines 8(5): 543-546.

Bailey M m, Mahoney C m, Dempah K e et al.: Fluorinated copolymer nanoparticles for multimodal imaging applications. Macromolecular Rapid Communications 31(1), 87-92 (2010).

Bollyky, P. L., J. D. Lord, et al. (2007). "Cutting edge: high molecular weight hyaluronan promotes the suppressive effects of CD4+CD25+ regulatory T cells." J Immunol 179(2): 744-747.

Bromley, S. K., A. Iaboni, et al. (2001). "The immunological synapse and CD28-CD80 interactions." Nat. Immunol. 2(12): 1159-1166.

Bullard, D. C., X. Hu, et al. (2007). "p150/95 (CD11c/CD18) expression is required for the development of experimental autoimmune encephalomyelitis." Am J Pathol 170(6): 2001-2008.

Bullard, D. C., X. Hu, et al. (2007). "Intercellular adhesion molecule-1 expression is required on multiple cell types for the development of experimental autoimmune encephalomyelitis." J Immunol 178(2): 851-857.

Byers, M. A., P. A. Calloway, et al. (2008). "Arrestin 3 mediates endocytosis of CCR7 following ligation of CCL19 but not CCL21." J Immunol 181(7): 4723-4732.

Cai, S., Y. Xie, et al. (2008). "Intralymphatic chemotherapy using a hyaluronan-cisplatin conjugate." J Surg Res 147 (2): 247-252.

Cai, S., Y. Xie, et al. (2009). "Pharmacokinetics and disposition of a localized lymphatic polymeric hyaluronan conjugate of cisplatin in rodents." J Pharm Sci.

Cairo, C. W., J. E. Gestwicki, et al. (2002). "Control of multivalent interactions by binding epitope density." J Am Chem Soc 124(8): 1615-1619.

Carter, P. H. and Q. Zhao (2010). "Clinically validated approaches to the treatment of autoimmune diseases." Expert Opin Investig Drugs 19(2): 195-213.

Cohen, M. S., S. Cai, et al. (2009). "A novel intralymphatic nanocarrier delivery system for cisplatin therapy in breast cancer with improved tumor efficacy and lower systemic toxicity in vivo." Am J Surg 198(6): 781-786.

Compston, A. and A. Coles (2002). "Multiple sclerosis." The Lancet 359(9313): 1221-1231.

de Sanjose, S., L. Alemany, et al. (2008). "Human papillomavirus vaccines and vaccine implementation." Womens Health (Lond Engl) 4(6): 595-604.

Dintzis, H. M., R. Z. Dintzis, et al. (1976). "Molecular determinants of immunogenicity: the immunon model of immune response." Proc Natl Acad Sci USA 73(10): 3671-3675.

Dintzis, H. M. D., R. Z. (1992). "Profound specific suppression by antigen of persistent IgM, IgG, and IgE antibody production." Proceedings of the National Academy of Sciences 89: 1113-1117.

Dintzis, R. Z., M. H. Middleton, et al. (1983). "Studies on the immunogenicity and tolerogenicity of T-independent antigens." J Immunol 131(5): 2196-2203.

Dintzis, R. Z., B. Vogelstein, et al. (1982). "Specific cellular stimulation in the primary immune response: experimental test of a quantized model." Proc Natl Acad Sci USA 79(3): 884-888.

Dixon, F. J. (1992). Advances in Immunology. San Diego, Academic Press, Inc.

Dustin, M. L. (2002). "The immunological synapse." Arthritis. Res. 4(Suppl 3): S119-125.

Dustin, M. L. (2009). "The cellular context of T cell signaling." Immunity 30(4): 482-492.

Dustin, M. L. and A. S. Shaw (1999). "Costimulation: Building an immunological synapse." Science 283(5402): 649-650.

Fraser, J. R.; Laurent, T. C.; Laurent, U. B. (1997). Hyaluronan: its nature, distribution, functions and turnover. J Intern Med, 242, (1), 27-33.

Gajewiak, J., S. Cai, et al. (2006). "Aminooxy Pluronics: Synthesis and Preparation of Glycosaminoglycan Adducts." Biomacromolecules 7(6): 1781-1789.

Gauthier, M. A. and H. A. Klok (2008). "Peptide/protein-polymer conjugates: synthetic strategies and design concepts." Chem Commun (Camb)(23): 2591-2611.

Gestwicki, J. E., C. W. Cairo, et al. (2002). "Influencing receptor-ligand binding mechanisms with multivalent ligand architecture." J Am Chem Soc 124(50): 14922-14933.

Goebel, S., M. Huang, et al. (2005). "VEGF-A Stimulation of Leukocyte Adhesion to Colonic Microvascular Endothelium: Implications for Inflammatory Bowel Disease." Am J Physiol Gastrointest Liver Physiol.

Hartman, N. C., J. A. Nye, et al. (2009). "Cluster size regulates protein sorting in the immunological synapse." Proc Natl Acad Sci USA 106(31): 12729-12734.

Heredia, K. L., Z. P. Tolstyka, et al. (2007). "Aminooxy End-Functionalized Polymers Synthesized by ATRP for Chemoselective Conjugation to Proteins." Macromolecules 40(14): 4772-4779.

Hu, X., J. E. Wohler, et al. (2009). "{beta}2-Integrins in demyelinating disease: not adhering to the paradigm." J Leukoc Biol.

Huang, M., K. Matthews, et al. (2005). "Alpha L-integrin I domain cyclic peptide antagonist selectively inhibits T cell adhesion to pancreatic islet microvascular endothelium." Am J Physiol Gastrointest Liver Physiol 288(1): G67-73.

Hwang, J., R. C. Li, et al. (2007). "Well-defined polymers with activated ester and protected aldehyde side chains for bio-functionalization." J Control Release 122(3): 279-286.

Inobe, J., A. J. Slavin, et al. (1998). "IL-4 is a differentiation factor for transforming growth factor-beta secreting Th3 cells and oral administration of IL-4 enhances oral tolerance in experimental allergic encephalomyelitis." Eur J Immunol 28(9): 2780-2790.

Johnston, C. T., S. L. Wang, et al. (2002). "Measuring the surface area of aluminum hydroxide adjuvant." J Pharm Sci 91(7): 1702-1706.

Kavanaugh, A. F., L. S. Davis, et al. (1996). "A phase I/II open label study of the safety and efficacy of an anti-ICAM-1 (intercellular adhesion molecule-1; CD54)

monoclonal antibody in early rheumatoid arthritis." J. Rheumatol. 23(8): 1338-1344.
Kobayashi, N., P. Kiptoo, et al. (2008). "Prophylactic and therapeutic suppression of experimental autoimmune encephalomyelitis by a novel bifunctional peptide inhibitor." Clin Immunol 129(1): 69-79.
Kobayashi, N., H. Kobayashi, et al. (2007). "Antigen-specific suppression of experimental autoimmune encephalomyelitis by a novel bifunctional peptide inhibitor." J Pharmacol Exp Ther 322(2): 879-886.
Kool, M., V. Petrilli, et al. (2008). "Cutting edge: alum adjuvant stimulates inflammatory dendritic cells through activation of the NALP3 inflammasome." J Immunol 181(6): 3755-3759.
Krejcova D, P. M., Safrankova B, Kubala L. (2009). "The effect of different molecular weight hyaluronan on macrophage physiology." Neuro Endocrinol Lett. 30((Suppl)): 106-111.
Krishnamoorthy, G., H. Lassmann, et al. (2006). "Spontaneous opticospinal encephalomyelitis in a double-transgenic mouse model of autoimmune T cell/B cell cooperation." J Clin Invest 116(9): 2385-2392.
Langer-Gould, A. and L. Steinman (2006). "Progressive multifocal leukoencephalopathy and multiple sclerosis: lessons from natalizumab." Curr Neurol Neurosci Rep 6(3): 253-258.
Link, H. (1998). "The cytokine storm in multiple sclerosis." Mult Scler 4(1): 12-15.
Lisak, R. P., B. Zweiman, et al. (1983). "Effect of treatment with Copolymer 1 (Cop-1) on the in vivo and in vitro manifestations of experimental allergic encephalomyelitis (EAE)." J Neurol Sci 62(1-3): 281-293.
Marc A. Gauthier and Harm-Anton Klok (2008). "ChemInform Peptide/Protein—Polymer Conjugates: Synthetic Strategies and Design Concepts." ChemInform 39(39).
Matsushita, T., K. Yanaba, et al. (2008). "Regulatory B cells inhibit EAE initiation in mice while other B cells promote disease progression." J Clin Invest 118(10): 3420-3430.
Mempel, T. R., S. E. Henrickson, et al. (2004). "T-cell priming by dendritic cells in lymph nodes occurs in three distinct phases." Nature 427(6970): 154-159.
Miller, S. D., D. M. Turley, et al. (2007). "Antigen-specific tolerance strategies for the prevention and treatment of autoimmune disease." Nat Rev Immunol 7(9): 665-677.
Moriyama, H., K. Yokono, et al. (1999). "Induction of tolerance in murine autoimmune diabetes by transient blockade of leukocyte function-associated antigen-1/intercellular adhesion molecule-1 pathway." J. Immunol. 157: 3737-3743.
Mossman, K. D., G. Campi, et al. (2005). "Altered TCR signaling from geometrically repatterned immunological synapses." Science 310(5751): 1191-1193.
Murray, J. S., S. Oney, et al. (2007). "Suppression of type 1 diabetes in NOD mice by bifunctional peptide inhibitor: modulation of the immunological synapse formation." Chem Biol Drug Des 70(3): 227-236.
Muto J, Y. K., Taylor K R, Gallo R L. (2009). "Engagement of CD44 by hyaluronan suppresses TLR4 signaling and the septic response to LPS" Mol Immunol. 47(2-3): 449-456.
Peek, L. J., C. R. Middaugh, et al. (2008). "Nanotechnology in vaccine delivery." Adv Drug Deliv Rev 60(8): 915-928.
Puffer, E. P., J. K. P., Jessica J. Hollenbeck, John A. Kink, and Laura L. Kiessling. (2006). Activating B Cell Signaling with Defined Multivalent Ligands. ACS Chemical Biology, 2, (4), 8.
Reichardt, P., B. Dornbach, et al. (2007). "The molecular makeup and function of regulatory and effector synapses." Immunol Rev 218: 165-177.
Reim, J. W., D. E. Symer, et al. (1996). "Low molecular weight antigen arrays delete high affinity memory B cells without affecting specific T-cell help." Mol Immunol 33(17-18): 1377-1388.
Reim, J. W. J. (1996). "Low molecular weight antigen arrays delete high affinity memory B cells without affecting specific T-cell help." Molecular immunology 33(17-18).
Renee Z. Dintzis, M. O., Marjorie H. Middleton, Gretchen Greene, and Howard M. Dintzis (1989). "The Immunogenicity of Soluble Haptenated Polymers is Determined by Molecular Mass and Hapten Valence." The Journal of Immunology 143(4): 5.
Ridwan, R., P. Kiptoo, et al. (2009). "Antigen-specific Suppression of Experimental Autoimmune Encephalomyelitis by a Novel Bifunctional Peptide Inhibitor: Structure Optimization and Pharmacokinetics." J Pharmacol Exp Ther.
Rolland, J. M., L. M. Gardner, et al. (2009). "Allergen-related approaches to immunotherapy." Pharmacol Ther 121(3): 273-284.
Sant, A. J., F. A. Chaves, et al. (2005). "The relationship between immunodominance, DM editing, and the kinetic stability of MHC class II:peptide complexes." Immunol Rev 207: 261-278.
Schulze-Koops, H., P. E. Lipsky, et al. (1995). "Elevated Th1- or Th0-like cytokine mRNA in peripheral circulation of patients with rheumatoid arthritis. Modulation by treatment with anti-ICAM-1 correlates with clinical benefit." J. Immunol. 155(10): 5029-5037.
Senti, G., B. M. Prinz Vavricka, et al. (2008). "Intralymphatic allergen administration renders specific immunotherapy faster and safer: a randomized controlled trial." Proc Natl Acad Sci USA 105(46): 17908-17912.
Sheridan, C. (2005). "Tysabri raises alarm bells on drug class." Nat Biotechnol 23(4): 397-398.
Shuang, C., X. Yumei, et al. (2008). "Intralymphatic Chemotherapy Using a Hyaluronan-Cisplatin Conjugate." The Journal of surgical research 147(2): 247-252.
Siliciano R F, C. R., Keegan A D, Dintzis R Z, Dintzis H M, Shin H S. (1985). "Antigen valence determines the binding of nominal antigen to cytolytic T cell clones." J Exp Med 162(2): 768-773.
Stebbings, R., L. Findlay, et al. (2007). ""Cytokine storm" in the phase I trial of monoclonal antibody TGN1412: better understanding the causes to improve preclinical testing of immunotherapeutics." J Immunol 179(5): 3325-3331.
Steinman, L. (2005). "Blocking adhesion molecules as therapy for multiple sclerosis: natalizumab." Nat Rev Drug Discov 4(6): 510-518.
Steinman, L. and P. Conlon (2001). "Antigen specific immunotherapy of multiple sclerosis." J Clin Immunol 21(2): 93-98.
Symer, D. E. D. (1995). "Durable elimination of high affinity, T cell-dependent antibodies by low molecular weight antigen arrays in vivo." Journal of immunology 155(12).
Tesar, B. M., D. Jiang, et al. (2006). "The Role of Hyaluronan Degradation Products as Innate Alloimmune Agonists." American Journal of Transplantation 6(11): 2622-2635.
Vines, C. M., J. W. Potter, et al. (2001). "Inhibition of beta 2 integrin receptor and Syk kinase signaling in monocytes by the Src family kinase Fgr." Immunity 15(4): 507-519.

Vines, C. M., C. M. Revankar, et al. (2003). "N-formyl peptide receptors internalize but do not recycle in the absence of arrestins." J Biol Chem 278(43): 41581-41584.

Wei BY, H.-S. V., Carter B G, Sehon A H. (1984). "Suppression of the anti-trimellityl (TM) IgE response in mice by conjugates of TM with polyvinyl alcohol." Immunology 51(4): 687-696.

Yanaba, K., J. D. Bouaziz, et al. (2008). "B-lymphocyte contributions to human autoimmune disease." Immunol Rev 223: 284-299.

Yanaba, K., J. D. Bouaziz, et al. (2009). "The development and function of regulatory B cells expressing IL-10 (B10 cells) requires antigen receptor diversity and TLR signals." J Immunol 182(12): 7459-7472.

Yanaba, K., Y. Hamaguchi, et al. (2007). "B cell depletion delays collagen-induced arthritis in mice: arthritis induction requires synergy between humoral and cell-mediated immunity." J Immunol 179(2): 1369-1380.

Yednock, T. A., C. Cannon, et al. (1992). "Prevention of experimental autoimmune encephalomyelitis by antibodies against alpha 4 beta 1 integrin." Nature 356(6364): 63-66.

M. Srinivasan, et al, "CD80 Binding Polyproline Helical Peptide Inhibits T Cell Activation," J. Biological Chemistry (2005).

K. Sandstrom, et al, "Inhibition of the CD28-CD80 co-stimulation signal by a CD28-binding affibody ligand developed by combinatorial protein engineering," Protein Eng (2003).

J. Chen, et al, "Allogenic donor splenocytes pretreated with antisense peptide against B7 prolong cardiac allograft survival," Clin Exp Immunology (2004)

T. Fukumoto, et al, "Peptide mimics of the CTLA4-binding domain stimulate T-cell proliferation," Nature Biotech (1998).

P. A. De Ciechi, et al, "Utilization of multiple phage display libraries for the identification of dissimilar peptide motifs that bind to a B7-1 monoclonal antibody," Mol Divers (1996)

What is claimed is:

1. A composition comprising:

a first conjugate comprising Signal-1 peptides bound to a first polymer carrier, wherein the first polymer carrier is a glycosaminoglycan, wherein the molecular weight of the first conjugate is from about 5 kDa to about 100 kDa, and wherein the size of the first conjugate is about 1 nanometer to about 10 nanometers.

2. The composition of claim 1 wherein the molecular weight of the first conjugate is about greater than 16.9 kDa to less than or equal to 80 kDa.

3. The composition of claim 1 wherein the molecular weight of the first conjugate is about 10 kDa to about 50 kDa.

4. The composition of claim 1 wherein the glycosaminoglycan is selected from the group consisting of: hyaluronic acid, chondroitin sulfate, dermatan sulfate, keratan sulfate, heparin, and heparin sulfate.

5. The composition of claim 1 wherein the Signal-1 peptides are insulin, PLP, MBP, MOG, GAD65 or are derived therefrom.

6. The composition of claim 1 further comprising a second conjugate comprising Signal-2 peptides bound to a second polymer carrier, wherein the second polymer carrier is a glycosaminoglycan, wherein the size of the second conjugate is about 1 nanometer to about 10 nanometers, and wherein no Signal-2 peptides are associated with the first conjugate and no Signal-1 peptides are associated with the second conjugate.

7. The composition of claim 6 wherein the Signal-2 peptides are an immune suppressor.

8. A method comprising administering to a subject in need thereof a therapeutically effective amount of composition comprising:

a first conjugate comprising Signal-1 peptides bound to a first polymer carrier, wherein the combined size of the first conjugate is about 1 nanometer to about 10 nanometers; and a second conjugate comprising Signal-2 peptides hound to a second polymer carrier wherein the size of the second conjugate is about 1 nanometer to about 10 nanometers, wherein the first polymer carrier and the second polymer carrier are each a glycosaminoglycan, and wherein no Signal-2 peptides are associated with the first conjugate and no Signal-1 peptides are associated with the second conjugate.

9. The method of claim 8 wherein the molecular weight of the first conjugate and the second conjugate are each about 5 kDa to about 100 kDa.

10. The method of claim 8 wherein the molecular weight of the first conjugate and the second conjugate are each about 10 kDa to about 50 kDa.

11. The method of claim 8 wherein the Signal-1 peptides and the Signal-2 peptides are bound to the first polymer carrier and the second polymer, respectively, via one or more oxime bonds derived from a reaction of a compound comprising an aminooxy group and a compound comprising amide group.

12. The method claim 8 wherein the first polymer carrier, the second polymer carrier or both comprise a polymer selected from the group consisting of: hyaluronic acid, chondroitin sulfate, dermatan sulfate, keratan sulfate, heparin and heparin sulfate.

13. The method of claim 8 wherein the Signal-1 peptides are PLP, MBP, MUG or GAD65.

14. The method of claim 8 wherein the Signal-2 peptides are LABL, cLABL, IBR, cIBR IBR7.

15. The method of claim 8 wherein the Signal-2 peptides are an immune suppressor.

16. The method of claim 8 wherein the subject has an auto-immune disease.

17. A method comprising:

providing a polymer carrier comprising at least one reactive amide or aminooxy group; providing a Signal-1 peptide comprising at least one reactive amide or aminooxy group or a Signal-2 peptide comprising at least one reactive amide and reacting the polymer carrier with the Signal-1 peptide or the Signal-2 peptide to form a conjugate via a A-oxime bond wherein the polymer carrier is a glycosaminoglycan.

18. The method of claim 17 wherein the polymer carrier comprises a polymer selected from the group consisting of: hyaluronic acid, chondroitin sulfate, dermatan sulfate, keratan sulfate, heparin and heparin sulfate.

19. The method of claim 17 wherein the size of the conjugate is about 1 nanometers to about 10 nanometers.

20. The method of claim 17 wherein the molecular weight of the conjugate is about 5 kDa to about 100 kDa.

21. The method of claim 17 wherein the molecular weight of the conjugate is about 10 kDa to about 50 kDa.

22. The method of claim 17 wherein the Signal-1 peptide is PLP, MBP, MOG or GAD65.

23. The method of claim 17 wherein the Signal-2 peptide is LABL, cLABL, IBR, cIBR, or IBR7.

24. The method of claim 17 wherein the Signal-2 peptide is an immune suppressor.

25. The composition of claim 6 wherein the Signal-2 peptides are LABL, cLABL, IBR, cIBR, or IBR7.

* * * * *